United States Patent
Whelan et al.

(10) Patent No.: US 9,974,545 B2
(45) Date of Patent: May 22, 2018

(54) SURGICAL CLAMPING DEVICES AND TOOLS FOR USE THEREWITH

(75) Inventors: Geoffrey Paul Whelan, Surrey Hills (AU); Abbas Kouzani, Highton (AU)

(73) Assignee: Surgiclamp Pty Ltd (AU)

( * ) Notice: Subject to any disclaimer, the term of this patent is extended or adjusted under 35 U.S.C. 154(b) by 1003 days.

(21) Appl. No.: 13/879,312

(22) PCT Filed: Oct. 17, 2011

(86) PCT No.: PCT/AU2011/001319
§ 371 (c)(1),
(2), (4) Date: Apr. 12, 2013

(87) PCT Pub. No.: WO2012/048387
PCT Pub. Date: Apr. 19, 2012

(65) Prior Publication Data
US 2014/0074122 A1    Mar. 13, 2014

(30) Foreign Application Priority Data

Oct. 15, 2010    (AU) ................................ 2010904622

(51) Int. Cl.
*A61B 17/08*    (2006.01)
*A61B 17/122*    (2006.01)
(Continued)

(52) U.S. Cl.
CPC ............ *A61B 17/122* (2013.01); *A61B 17/12* (2013.01); *A61B 17/1285* (2013.01);
(Continued)

(58) Field of Classification Search
CPC ... A61B 17/122; A61B 17/1285; A61B 17/12; A61B 2017/0046; A61B 2017/00477;
(Continued)

(56) References Cited

U.S. PATENT DOCUMENTS

| 5,207,691 A | 5/1993 | Nardella |
| 5,258,007 A | 11/1993 | Spetzler |

(Continued)

FOREIGN PATENT DOCUMENTS

| CN | 101530340 A | 2/2009 |
| EP | 1878390 A1 | 7/2006 |

(Continued)

OTHER PUBLICATIONS

International Search Report from corresponding PCT/AU2011/001319.

(Continued)

*Primary Examiner* — Katrina Stransky
*Assistant Examiner* — Kankindi Rwego
(74) *Attorney, Agent, or Firm* — Tarolli, Sundheim, Covell & Tummino LLP

(57) ABSTRACT

Embodiments of the present invention relate to surgical clamping devices and applicators for use therewith. Embodiments of the surgical clamping device comprise a body and a pair of clamping members extending from the body. An electronic controller housed within the body is coupled to control movement of at least one of the clamping members to control a pressure exerted by the clamping members on a blood vessel clamped therebetween. At least one blood flow sensor is mounted to at least one of the clamping members to detect blood flow in the blood vessel. The clamping members are locked in place when blood flow has been occluded or constricted to the desired extent.

19 Claims, 17 Drawing Sheets

(51) Int. Cl.
*A61B 17/12* (2006.01)
*A61B 17/128* (2006.01)
*A61B 17/00* (2006.01)

(52) U.S. Cl.
CPC ............... *A61B 2017/00022* (2013.01); *A61B 2017/0046* (2013.01); *A61B 2017/00398* (2013.01); *A61B 2017/00477* (2013.01); *A61B 2017/00734* (2013.01); *A61B 2017/12004* (2013.01)

(58) Field of Classification Search
CPC ........... A61B 2017/12004; A61B 2017/00398; A61B 2017/00022; A61B 2017/00734; A61B 17/320092; A61B 17/3207; A61B 17/064; A61B 17/068; A61B 17/08; A61B 17/10; A61B 17/28; A61B 17/29; A61B 2017/2926; A61B 2017/2927; A61B 2017/2929; A61B 2017/293; A61B 2017/2931; A61B 2017/2932; A61B 2017/2933; A61B 2017/2934; A61B 2017/2936; A61B 2017/2937; A61B 2017/2938; A61B 2017/2939; A61B 2017/294; A61B 2017/2941; A61B 2017/2943; A61B 2017/2944; A61B 2017/2945; A61B 2017/2947; A61B 2017/2948; A61B 34/30; A61B 34/74; A61B 2034/741; A61B 2034/742; A61B 2034/743; A61B 2034/744
See application file for complete search history.

(56) References Cited

U.S. PATENT DOCUMENTS

| | | | |
|---|---|---|---|
| 5,458,387 A * | 10/1995 | Conway | B25J 7/00 294/100 |
| 5,921,996 A | 7/1999 | Sherman | |
| 2002/0183771 A1* | 12/2002 | Burbank | A61B 5/415 606/158 |
| 2003/0028217 A1* | 2/2003 | Nakamura | A61B 17/29 606/205 |
| 2004/0143263 A1* | 7/2004 | Schechter | A61B 17/122 606/51 |
| 2005/0113634 A1 | 5/2005 | Burbank et al. | |
| 2005/0131390 A1* | 6/2005 | Heinrich | A61B 17/0469 606/1 |
| 2005/0209614 A1* | 9/2005 | Fenter | A61B 17/11 606/153 |
| 2005/0277959 A1 | 12/2005 | Cosgrove et al. | |
| 2007/0038115 A1* | 2/2007 | Quigley | A61N 7/02 600/471 |
| 2007/0173814 A1* | 7/2007 | Hixson | A61B 18/1445 606/51 |
| 2008/0287926 A1 | 11/2008 | El Kheir | |

FOREIGN PATENT DOCUMENTS

| | | |
|---|---|---|
| WO | WO 1997/010764 A1 | 3/1997 |
| WO | 03082129 A2 | 10/2009 |

OTHER PUBLICATIONS

Extended European Search Report dated Jul. 17, 2014, pp. 1-11.
Chinese Search Report dated Nov. 17, 2014, pp. 1-3.

* cited by examiner

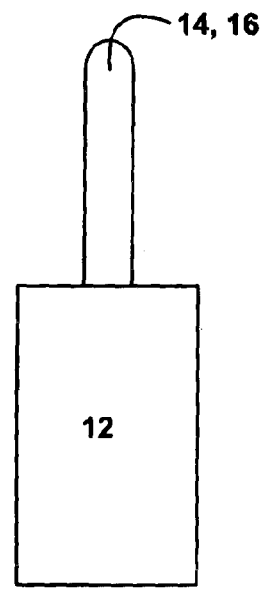
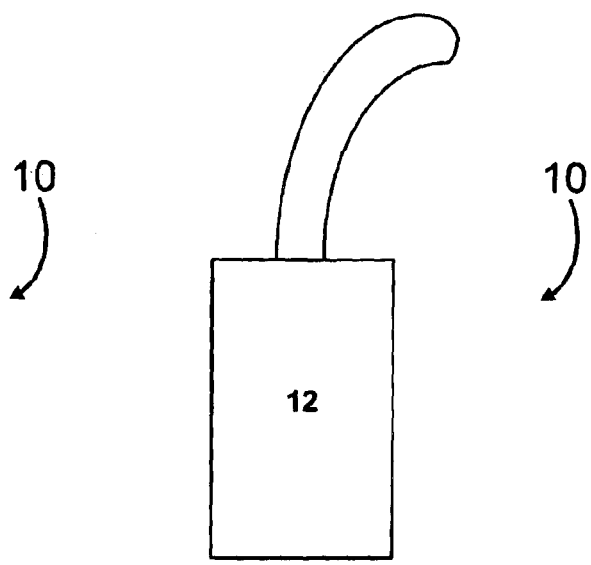
FIG 3A                    FIG 3B
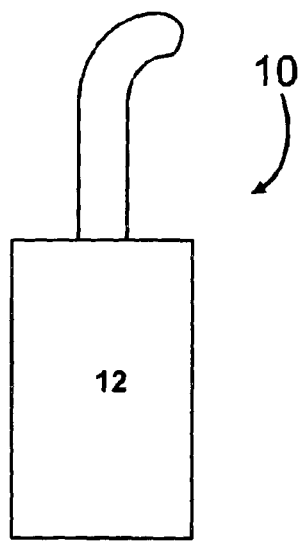 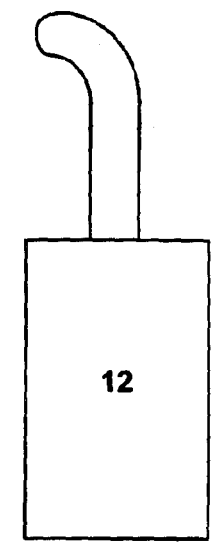 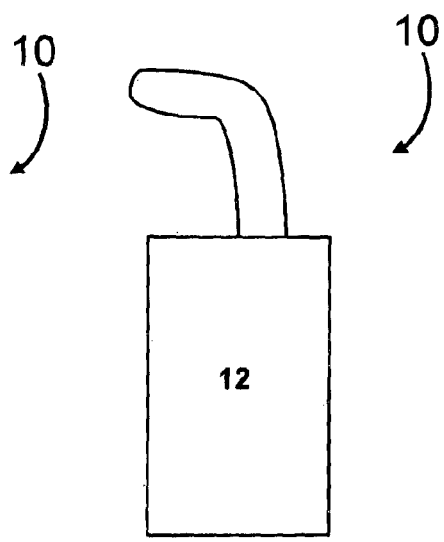
FIG 3C          FIG 3D          FIG 3E

SURGICAL CLAMPING DEVICES AND TOOLS FOR USE THEREWITH

FIELD OF THE INVENTION

The present invention relates to surgical clamping devices and tools for use therewith. In particular, but not exclusively, the present invention relates to devices for constricting and/or occluding blood flow in blood vessels, such as veins, arteries and capillaries in humans and animals. The present invention also relates to tools that can be used with the surgical clamping devices.

BACKGROUND OF THE INVENTION

During many surgical procedures it is necessary to temporarily constrict or occlude the blood flow in blood vessels, such as veins and arteries. This is typically achieved with a surgical clamp comprising a pair of elongate clamping members. A clamping member is positioned either side of the vein or artery, or either side of body tissue comprising the vein or artery, and the clamping members are biased towards each other to hold the vein, artery or body tissue therebetween. Biasing is typically achieved via a spring, a ratcheting mechanism or by hand depending on the type of clamping device and the location of the vein, artery or body tissue being clamped.

Blood vessel clamps, for example, are available from manufacturers in a range of sizes suited to clamping blood vessels ranging from about 0.2 mm to about 12.0 mm. Some clamps have a pre-set clamping tension for each respective clamp size, while other larger clamps are manually operated using a ratcheting closure system requiring the operator to estimate the appropriate level of force required to occlude blood flow in the blood vessel. Smaller clamps comprise shorter clamping members and smaller springs, which exert a lower clamping force in an effort to avoid damage to the respective blood vessels. Conversely, larger clamps comprise longer clamping members and stronger springs, which exert a higher clamping force to constrict or occlude blood flow in larger blood vessels. Such clamps can be single clamps or a pair of clamps mounted to a rod or pin and spaced apart for clamping two different locations of a single artery.

For other types of surgery, the pair of elongate clamping members is provided at the end of a pair of elongate handles, such as with forceps, such that clamping within a body cavity can be achieved more easily. In this example, the clamping members are typically retained in one of a plurality of predetermined separation positions via a releasable ratchet mechanism.

One disadvantage with the aforementioned prior art clamping devices is that the force exerted on the vein, artery or tissue by the clamping members can vary quite significantly. This will depend on the size and type of clamp used, the size and type of spring or other biasing means employed, the type of vein or artery being clamped and the amount and type of tissue surrounding the vein or artery. For example, muscle has a high tensile strength whereas fat has a low tensile strength. If the force is too low, the desired level of blood flow constriction or occluded blood flow will not be achieved and if the force is too high, the vein or artery could be damaged leading to potentially life-threatening complications. Examples of such complications include thrombosis, which is caused as a result of damage to the blood vessel at the point of clamping, and heart attacks or strokes caused by dislodgement of plaque material at the clamping site.

Often the pressure exerted by the clamping members is non-uniform along their length resulting in a pressure gradient. Many clamps apply greater pressure at the approximate location of the blood vessel being clamped with less pressure being applied at the distal location of the blood vessel causing damage to the blood vessel as a result of uneven pressure being applied to the blood vessel.

Another drawback of the conventional surgical clamps and in particular the manually operated clamps that are available in a range of sizes and shapes, is the cost. For example, a batch of 10 surgical clamps of a single size and shape can cost about $500. A single size of clamp may only be suitable for a specific type of surgery and such clamps are often disposable, single-use clamps. Therefore medical facilities experience significant expenditure in providing and maintaining sufficient numbers of clamps in the required range of sizes. Furthermore, a particular size of clamp may be suitable for exerting an appropriate level of force on a particular artery in one patient, but this may be excessive or insufficient for the same artery in the same procedure in a different patient, for example, due to varying levels of plaque build up between patients.

Metal surgical clamping devices can be sterilized and reused, which addresses to an extent the cost associated with replacing single use clamping devices. However, reusable metal surgical clamping devices usually have a greater initial cost. Also, at least some of the metal surgical clamping devices experience metal fatigue after repeated use, which can lead to cracks in the metal that can cause infection. Metal surgical clamps also tend to lose clamping tension due to repeated use.

Various attempts have been made to alleviate at least some of these problems. For example, European Patent No. EP 1 562 492 discloses an apparatus for the detection and occlusion of blood flow comprising a pair of elongate clamping members for clamping tissue comprising an artery. The apparatus is similar to a pair of forceps and comprises a releasable ratcheting mechanism to maintain pressure between the clamping members. One of the clamping members comprises a blood flow detecting sensor to facilitate the location or monitoring of the artery to be occluded. The sensor can detect the reduction or abolition of blood flow and the releasable ratcheting mechanism can be adjusted to change the blood flow.

The apparatus of EP 1 562 492 is particularly suited for occluding blood flow in uterine arteries. However, blood flow is still dependent on and controlled by the manual adjustment of the releasable ratcheting mechanism by the nurse or surgeon, thus still requiring the necessary skill and care in applying the correct pressure for the particular procedure, the particular region of the body and the particular patient. Furthermore, the blood flow detecting sensor is coupled to a sensor control device via a detachable cable external to the elongate arms of the device. The external cable can potentially interfere with the procedure and can present a snagging risk in relation to other apparatus or protruding elements in the operating theatre. Therefore, the external cable is considered an undesirable feature. Whilst the elongate arms facilitate access to body cavities, the elongate arms render the clamping apparatus of EP 1 562 492 unusable for many procedures where clamping in confined cavities is required.

Other clamping or occlusion devices are known from the following: US 2005/0113634, US 2005/0113852, WO 2009/048367, U.S. Pat. No. 6,582,451, U.S. Pat. No. 6,656,205, U.S. Pat. No. 4,120,302 and U.S. Pat. No. 5,697,942.

However, at least, some of the clamping or occlusion devices in these documents exhibit one or more of the aforementioned problems.

The reference to any prior art in this specification is not, and should not be taken as, an acknowledgement or any form of suggestion that the prior art forms part of the common general knowledge.

OBJECT OF THE INVENTION

It is a preferred object of the invention to provide an improved surgical clamping device that addresses or ameliorates one or more of the aforementioned problems of the prior art or provides a useful commercial alternative.

It is another preferred object of the invention to provide a tool for use with the improved surgical clamping devices.

SUMMARY OF THE INVENTION

Generally, the present invention relates to surgical clamping devices wherein a predetermined clamping force can be achieved and/or the likelihood of damage to the blood vessel being clamped is minimized or at least reduced compared with the prior art. Generally, the present invention also relates to tools for use with the surgical clamping devices.

According to one aspect, the present invention resides in a surgical clamping device comprising:
 a body; and
 a pair of elongate clamping members extending from the body wherein a shape of the elongate clamping members is adjustable.

Preferably, the elongate clamping members are made from a flexible material allowing the shape of the elongate clamping members to be conformed to the blood vessel to be clamped.

Suitably, the elongate clamping members are integrally formed with the body.

Suitably, the elongate clamping members are detachable from the body.

According to another aspect, the present invention resides in a surgical clamping device comprising:
 a body; and
 a pair of elongate clamping members extending from the body wherein an angle of the elongate clamping members relative to the body is adjustable.

Suitably, the elongate clamping members are adjustable relative to the body in a vertical plane.

Suitably, the elongate clamping members are adjustable relative to the body in a horizontal plane.

Suitably, the elongate clamping members can occupy one of a plurality of predetermined angles relative to the body.

Alternatively, the elongate clamping members can occupy any position within a predetermined range of angles.

The body may comprise a ratchet mechanism or gearing mechanism for securing the elongate clamping members at the predetermined angles.

In the aforementioned aspects, a length of the elongate clamping members is selectable from a plurality of predetermined lengths.

According to a further aspect, the present invention resides in a surgical clamping device comprising:
 a body;
 a pair of elongate clamping members extending from the body; and
 a controller housed within the body and coupled to the elongate clamping members for controlling the pressure exerted by the elongate clamping members on a blood vessel clamped therebetween.

Preferably, the body comprises at least one actuator coupled to the controller wherein actuation of the at least one actuator causes the controller to increase or decrease the pressure exerted by the elongate clamping members.

Suitably, the body comprises a first pair of opposed actuators coupled to the controller wherein actuation of the first pair of opposed actuators causes the controller to increase the pressure exerted by the elongate clamping members.

Suitably, the body comprises a second pair of opposed actuators coupled to the controller wherein actuation of the second pair of opposed actuators causes the controller to decrease the pressure exerted by the elongate clamping members.

Suitably, the first pair of opposed actuators are perpendicular to the second pair of opposed actuators. Suitably, the first and second pair of opposed actuators are operated by the thumb and forefinger of a user.

Preferably, the controller adjusts a position of one or both of the elongate clamping members such that a pressure is exerted on the blood vessel clamped therebetween sufficient to constrict or occlude blood flow as required.

Suitably, the controller is implemented via a micro-electro-mechanical-system (MEMS).

Suitably, the elongate clamping members are detachable from the body. The elongate clamping members and/or the body may be disposable for single use or may be reusable.

Suitably, at least one blood flow sensor is mounted to one of the elongate clamping members to detect blood flow in the blood vessel clamped between the elongate clamping members.

Preferably, the elongate clamping members either side of the blood vessel are locked in place once the at least one blood flow sensor detects that blood flow has been occluded or constricted to the desired extent.

Suitably, the at least one blood flow sensor is implemented using Coriolis technology.

Suitably, the at least one blood flow sensor is coupled to an output device for displaying an indication of the blood flow via a wired or wireless link.

Suitably, the at least one blood flow sensor detects a calibre of the blood vessel clamped between the elongate clamping members.

Suitably, at least one sensor is mounted to at least one of the elongate clamping members to detect a mass of the blood vessel clamped between the elongate clamping members, wherein the controller adjusts a pressure applied by the elongate clamping members according to the detected mass.

One or more of the elongate clamping members of one or more of the aforementioned embodiments may comprise a non-slip coating to prevent the blood vessel from sliding from a clamping surface of the elongate clamping members.

One or more of the elongate clamping members of one or more of the aforementioned embodiments may comprise a channel for receiving the blood vessel. One of the elongate clamping members may comprise a projection aligned with the channel in the other elongate clamping members to securely clamp the blood vessel in position.

According to another aspect, the present invention resides in an applicator for use with a surgical clamping device, the applicator comprising:
 a body housing at least one input device; at least one output device and a microcontroller coupled to the input and output devices;

an arm connected to the body at a proximal end; and
a head at a distal end of the arm for connection to the surgical clamping device, the head in communication with the microcontroller.

Suitably, the arm comprises a cylindrical sleeve member connected to the body and an elongation member housed within the cylindrical sleeve member.

A linear actuator may control extension and retraction of the elongation member relative to the cylindrical sleeve member.

The head may comprise a frame supporting a ball member which can pan and tilt relative to the frame, the ball member comprising an interface for coupling the surgical clamping device to the head.

Suitably, the arm of the applicator is flexible.

According to another aspect, the present invention resides in an applicator for use with a surgical clamping device, the applicator comprising:

a body housing at least one input device, at least one output device, a micro-motor and a microcontroller coupled to the input and output devices and the micro-motor;
an actuation mechanism coupled to the micro-motor;
an arm connected to the body at a proximal end; and
a connecting rod housed within the arm, a proximal end of the connecting rod coupled to the actuation mechanism and a distal end connectable to the surgical clamping device.

Preferably, the connecting rod can be rotated bi-directionally in a clockwise and anticlockwise direction and extended and retracted.

Suitably, a distal end of the arm comprises one or more electrodes for connection with respective electrodes of the surgical clamping device and/or a recess for receiving a mounting guide of the surgical clamping device.

The applicators preferably comprise an electromagnetic system controlled by the microcontroller for controlling connection and disconnection of the surgical clamping device and the applicator.

Further aspects and features of the present invention will become apparent from the following detailed description.

BRIEF DESCRIPTION OF THE DRAWINGS

In order that the invention may be readily understood and put into practical effect, reference will now be made to preferred embodiments of the present invention with reference to the accompanying drawings, wherein like reference numbers refer to identical elements. The drawings are provided by way of example only, wherein:

FIG. 3A is a schematic plan view of a surgical clamping device according to a third embodiment showing flexible clamping members in a first arrangement;

FIG. 3B is a schematic plan view of the surgical clamping device of FIG. 3A showing the flexible clamping members in a second arrangement;

FIG. 3C is a schematic plan view of the surgical clamping device of FIG. 3A showing the flexible clamping members in a third arrangement;

FIG. 3D is a schematic plan view of the surgical clamping device of FIG. 3A showing the flexible clamping members in a fourth arrangement;

FIG. 3E is a schematic plan view of the surgical clamping device of FIG. 3A showing the flexible clamping members in a fifth arrangement;

Figure 1:
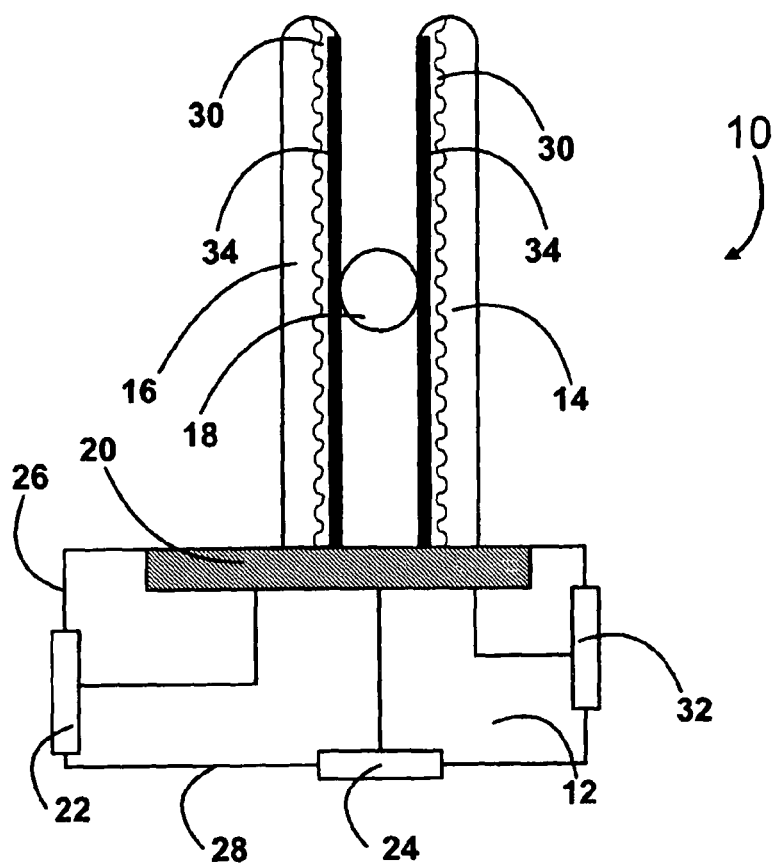
FIG. 1 is a schematic side view of a surgical clamping device according to a first embodiment of the present invention.

Skilled addressees will appreciate that elements in the drawings are illustrated for simplicity and clarity and have not necessarily been drawn to scale. For example, the relative dimensions of some of the elements in the drawings may be distorted to help improve understanding of embodiments of the present invention.

DETAILED DESCRIPTION OF THE PREFERRED EMBODIMENTS

With reference to FIG. 1, an improved surgical clamping device 10 according to an embodiment of the present invention comprises a body 12 and a pair of elongate clamping members 14, 16 extending from the body for clamping a blood vessel 18, such as an artery, vein or capillary. This embodiment also comprises a controller 20 housed within the body and coupled to the elongate clamping members for controlling the pressure exerted by the elongate clamping members 14, 16 on a blood vessel 18 clamped between the elongate clamping members.

According to some embodiments, the body 12 comprises at least one actuator 22 coupled to the controller 20 wherein actuation of the at least one actuator 22 causes the controller 20 to increase or decrease the pressure exerted by the elongate clamping members 14, 16.

In the embodiment shown in FIG. 1, two actuators 22, 24 are provided. Body 12 comprises a first actuator 22 coupled to the controller 20 wherein actuation of the first actuator 22 by a user causes the controller to increase the pressure exerted by the elongate clamping members 14, 16 by causing the separation between the elongate clamping members to be reduced. Body 12 comprises a second actuator 24 coupled to the controller 20 wherein actuation of the second actuator 24 causes the controller to decrease the pressure exerted by the elongate clamping members 14, 16 by increasing the separation between the elongate clamping members. Varying the separation between the elongate clamping members 14, 16 can be achieved by moving one or both of the elongate clamping members. In this embodiment, first actuator 22 is provided on, or mounted within, a first wall 26 of the body 12 and second actuator 24 is provided on, or mounted within, a second wall 28 of the body. However, other configurations of the first and second actuators 22, 24 are envisaged depending on the size and shape of the body 12 and the particular procedure(s) for which the improved surgical clamping device 10 is intended.

According to some embodiments, the controller 20 and the components to effect movement of the elongate clamping members 14, 16 are implemented via a micro-electro-mechanical-system (MEMS), as will be described in detail herein. For example, movement of the elongate clamping members can be effected by a micro-scale gearing or ratcheting system controlled by a microchip within the body 12 or external to the body via a wired or wireless link. The microchip is pre-programmed and coupled to be in communication with the elongate clamping members 14, 16, controller 20, actuators 22, 24, blood flow sensor 30 and one or more other sensors, output device 32, limiter and external patient monitoring device as described herein. It will be appreciated that the body 12 can also comprise a suitable power supply to power the components therein.

The improved surgical clamping device 10 further comprises at least one blood flow sensor 30 mounted to, or integrated with, one of the elongate clamping members 14, 16 to detect blood flow in the blood vessel 18 clamped between the elongate clamping members. The blood flow sensor 30 can be implemented via both elongate clamping members 14, 16 as illustrated in FIG. 1. The blood flow sensor 30 can be coupled to an output device 32, such as an LCD screen or seven segment display, mounted to, or within, the body 12 for displaying an indication of the blood flow. The blood flow sensor 30 can be coupled to output device 32 via a wired connection via the controller 20/MEMS. Alternatively, the blood flow sensor 30 can be coupled to output device 32 wirelessly. In some embodiments, the output device 32 is not provided on the body 12 of the improved surgical clamping device 10. In such embodiments, the output device of a conventional patient monitoring device can be utilized with blood flow data being communicated to the conventional patient monitoring device wirelessly.

The blood flow sensor 30 can be selected from sensors consisting of pressure sensors, magnetic sensors, electrical sensors, optical sensors, nuclear sensors, strain sensors, stress sensors, acoustic sensors, ultrasound sensors, such as Doppler ultrasound sensors, electromagnetic radiation sensors, chemical sensors, thermal sensors, Coriolis micro flow sensors and combinations thereof.

Although the blood flow sensor 30 is generally indicated in FIG. 1 as being provided along substantially the full length of the elongate clamping members 14, 16, the positioning of the blood flow sensor 30 on the elongate clamping members 14, 16 and the proportion of the length of the elongate clamping members along which the blood flow sensor 30 is provided will depend on the type(s) of blood flow sensor employed.

According to some embodiments, the at least one blood flow sensor 30 detects a calibre of the blood vessel 18 clamped between the elongate clamping members. In other words, the quality or Condition of the blood vessel can be detected. The calibre of the same vein or artery can vary quite widely between patients due to a range of factors. For example, arteriosclerotic vascular disease (ASVD) or atherosclerosis causes artery walls to thicken as the result of a build-up of fatty materials. A different clamping pressure is required for arteries affected by this condition compared with arteries not so affected. For example, a Doppler ultrasound sensor can detect thickening of the artery walls and the controller 20/MEMS can factor in the detected thickness into the determination of the pressure to be exerted by the elongate clamping members 14, 16.

According to some embodiments, at least one sensor is mounted to at least one of the elongate clamping members 14, 16 to detect a mass of the blood vessel clamped between the elongate clamping members. The mass of the same blood vessel in the same location can vary between patients depending on a range of factors, such as the age and condition of the patient and whether any conditions are presenting, such as ASVD referred to above. Therefore, the pressure required to occlude the same blood vessel can vary between patients. Therefore, the controller 20 adjusts a pressure applied by the elongate clamping members 14, 16 according to the detected mass of the blood vessel.

One or more of the elongate clamping members 14, 16 can comprise a non-slip coating or layer 34 on at least part thereof to prevent the blood vessel 18 from sliding from a clamping surface of the elongate clamping members. In the embodiment shown in FIG. 1, non-slip coating or layer 34 is provided on both elongate clamping members 14, 16. Non-slip coating or layer 34 can also be softer than the remainder of the elongate clamping members 14, 16 to help reduce or avoid trauma to the blood vessel 18. Alternatively, a soft cushioning layer or surface can be provided on, or applied to, the harder elongate clamping members 14, 16 and if required, the soft cushioning layer can have a further non-slip coating or layer 34 applied thereto. As a further alternative, a surface of the soft cushioning layer can be treated to render it non-slip.

Figure 2:
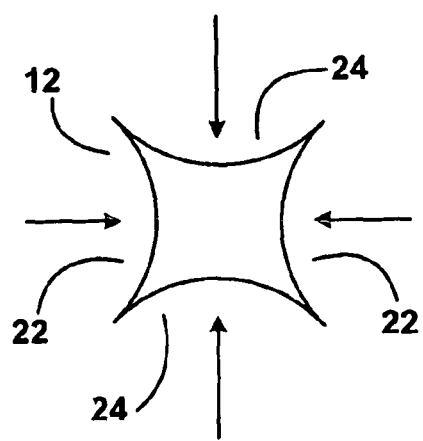
FIG. 2 is a schematic end view of a body of a surgical clamping device according to a second embodiment of the present invention.

Referring to FIG. 2, according to a second embodiment, body 12 comprises a first pair of opposed actuators 22 mounted thereto and coupled to the controller 20 wherein actuation of the first pair of opposed actuators as indicated by the arrows causes the controller 20 to increase the pressure exerted by the elongate clamping members 14, 16. Body 12 also comprises a second pair of opposed actuators 24 mounted thereto and coupled to the controller 20 wherein actuation of the second pair of opposed actuators as indicated by the arrows causes the controller to decrease the pressure exerted by the elongate clamping members 14, 16. As shown in FIG. 2, the first pair of opposed actuators 22 are substantially perpendicular to the second pair of opposed actuators 24. The first and second pair of opposed actuators 22, 24 can be conveniently operated with the thumb and forefinger of a user alternately to increase or decrease the pressure exerted by the elongate clamping members as required.

The controller 20 adjusts a position of one or both of the elongate clamping members 14, 16 such that a pressure is exerted on the blood vessel 18 clamped therebetween sufficient to constrict or occlude blood flow as required. The current blood flow can be indicated by the output device 32 as described above such that the operator can increase or decrease the pressure via actuators 22, 24 as desired.

The controller 20/MEMS includes a limiter that prevents the pressure exerted by the elongate clamping members 14, 16 exceeding a level that would cause trauma to the blood vessel 18 being clamped. The pressure level limit can be determined based on the detected blood flow and/or the detected calibre and/or the detected mass of the blood vessel 18 as described above. The limiter also prevents the separation of the elongate clamping members 14, 16 exceeding the physical limits of the device 10.

With reference to FIGS. 3A to 3B, according to other embodiments of the improved surgical clamping device 10, the shape of the elongate clamping members 14, 16 is adjustable. The elongate clamping members are made from a flexible material allowing the shape of the elongate clamping members to be conformed to the blood vessel 18 to be clamped. FIG. 3A shows the elongate clamping members in a linear arrangement as shown in the previous embodiments. FIG. 3B shows the elongate clamping members curved to the right along substantially the whole length of the elongate clamping members. FIG. 3C shows the elongate clamping members 14, 16 curved to the right at the tips thereof distal from the body 12. FIG. 3D shows the elongate clamping members 14, 16 curved to the left at the tips thereof, but at a different angle from that shown in FIG. 3C. FIG. 3D shows the elongate clamping members 14, 16 bent to the left approximately at a mid-point thereof, such that the elongate clamping members 14, 16 are at an angle of about 100°. The adjustable elongate clamping members enable the improved surgical clamping device 10 to be adapted to a range of different blood vessels, a range of different sizes of blood vessels, a range of different locations within the animal or human body and to use in a range of different surgical procedures. Hence, a single version of the improved surgical clamping device 10 can avoid or reduce the need for a wide range of different clamping devices that are dedicated to a single type/size/location of blood vessel or to one or only a limited number of surgical procedures.

Figure 4A:
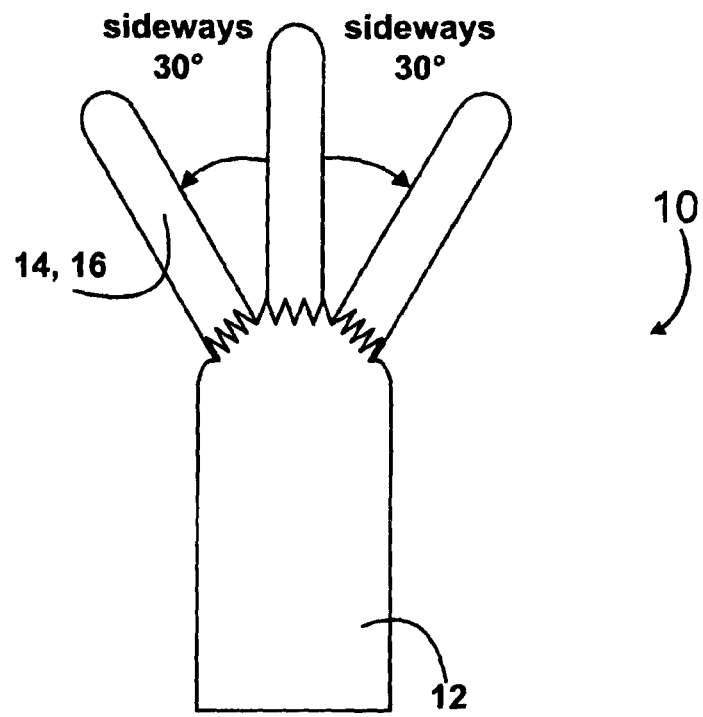
FIG. 4A is schematic plan view of a surgical clamping device according to a fourth embodiment showing clamping members at different angles in a horizontal plane.
Figure 4B:
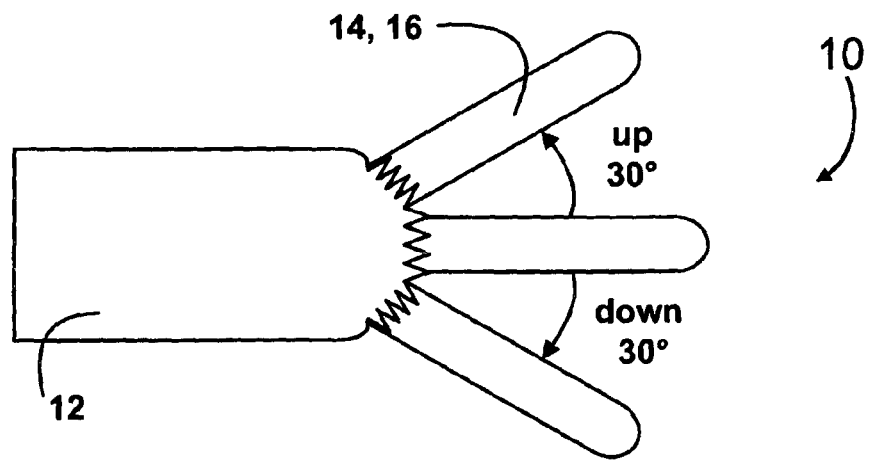
FIG. 4B is schematic side view of the surgical clamping device of FIG. 4A showing clamping members at different angles in a vertical plane.

With reference to FIGS. 4A and 4B, according to other embodiments of the improved surgical clamping device 10, an angle of the elongate clamping members 14, 16 extending from the body 12 is adjustable. As shown in the plan view in FIG. 4A, the elongate clamping members can be adjustable relative to the body in a horizontal plane. Alternatively, as shown in the side view in FIG. 4B, the elongate clamping members are adjustable relative to the body in a vertical plane. In a further alternative embodiment, the elongate clamping members 14, 16 can be adjustable relative to the body 12 in both a vertical and horizontal plane.

According to some embodiments, the elongate clamping members 14, 16 can occupy one of a plurality of predetermined angles relative to the body 12. According to other embodiments, the elongate clamping members can occupy any position within a predetermined range of angles. FIG. 4A shows the elongate clamping members occupying three different positions in the same horizontal plane—a central position, a position 30° left of the central position and a position 30° right of the central position. FIG. 4B shows the elongate clamping members occupying three different positions in the same vertical plane—a central position, a position 30° above the central position and a position 30° below the central position. It will be appreciated that many other angles are achievable whether such angles are discrete predetermined positions or any position within a predetermined range of angles. For example, in some embodiments the elongate clamping members may be able to occupy any position 90° either side of the central position providing a 180° range of positions. The body may comprise a ratchet mechanism or gearing mechanism for securing the elongate clamping members 14, 16 at the different angles relative to the body. Alternatively, a locking mechanism can be employed which secures the elongate clamping members at the desired angle.

Figure 5A:
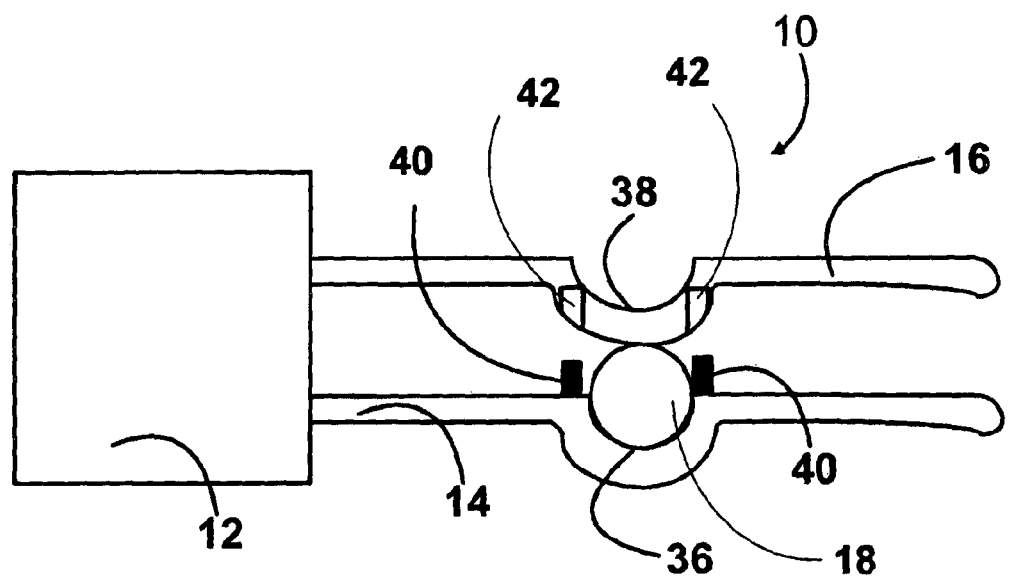
FIG. 5A is a schematic side view of a further embodiment of the surgical clamping device showing clamping members with a channel.
Figure 5B:
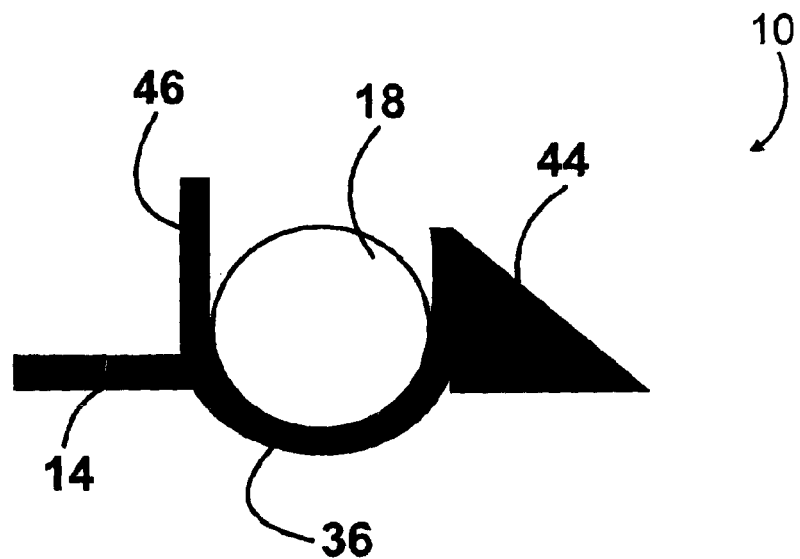
FIG. 5B is a schematic side view of a further embodiment of the surgical clamping device showing a clamping member with a channel and an inclined portion.
Figure 5C:
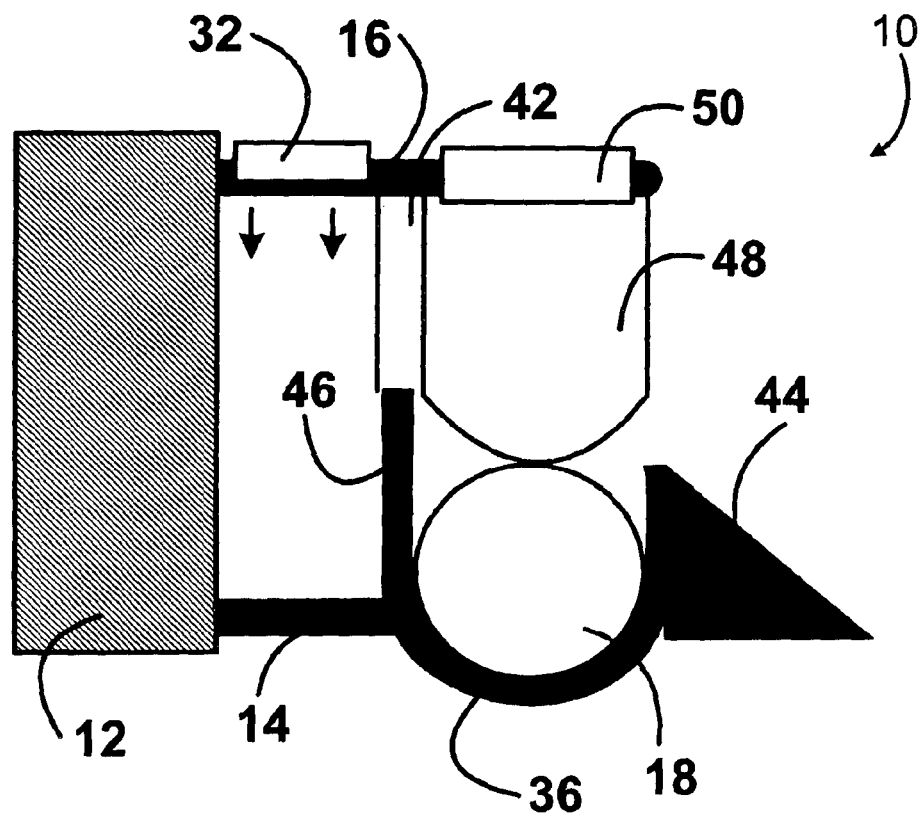
FIG. 5C is a schematic side view of a further embodiment of the surgical clamping device comprising a magnifying device, output device and alignment recess.

Referring to FIGS. 5A-5C, one or more of the elongate clamping members 14, 16 of one or more of the aforementioned embodiments can comprise a recess or channel 36 for receiving the blood vessel 18. The channel 36 in clamping member 14 shown in FIG. 5A retains the blood vessel in position and prevents the blood vessel from moving along the length of the elongate clamping members. According to some embodiments, the elongate clamping member that does not comprise the recess or channel 36 can be linear as shown in FIG. 1 and described above.

According to other embodiments and as shown in FIG. 5A, the elongate clamping member 16 that does not comprise the recess or channel 36 for receiving the blood vessel 18 can comprise a recess or channel 38 aligned with the channel 36 in the other elongate clamping member 14 to securely clamp the blood vessel 18 in position. The recess or channel 38 curves in the same direction as channel 36 and the underside of channel 38 contacts the blood vessel 18 in channel 36 and applies pressure thereto to constrict or occlude the blood flow.

In other embodiments, the channel 38 can be inverted such that channels 36, 38 form a substantially circular aperture that surrounds the blood vessel 18 when the elongate clamping members 14, 16 are closed together.

In some embodiments, the channel 36 and/or the channel 38 comprise the non-slip coating or layer 34 described above.

According to some embodiments of the improved surgical clamping device 10, elongate clamping member 14 comprises a projection 40 either side of the channel 36. Elongate clamping member 16 comprises a recess 42 either side of the channel 38 sized and shaped to receive a respective projection 40 of the elongate clamping member 14. During closure of the elongate clamping members 14, 16, recesses 42 receive respective projections 40 therein and once fully accommodated prevent further closure of the elongate clamping members 14, 16. Hence, each projection and recess pair determines a minimum separation for the clamping members 14, 16. The extent of the projections 40 and the depth of the recesses 42 are such that they prevent trauma to the blood vessel 18 being clamped. The size of the projections 40 and recesses 42 may vary between different embodiments according to the particular vein or artery or capillary being clamped and/or the particular surgical procedure(s) for which the improved surgical clamping device 10 is/are intended. It is envisaged that the projections 40 and recesses 42 can be provided at other positions along the length of the elongate clamping members 14, 16 and need not necessarily be provided adjacent or within the channels 36, 38 as shown in FIG. 5A.

FIG. 5B shows an alternative embodiment of the elongate clamping member 14, which comprises channel 36 for receiving the blood vessel 18. In this embodiment, the elongate clamping member 14 comprises an inclined portion 44 from a tip of the clamping member 14 to the channel 36 to facilitate location of the blood vessel 18 into the channel 36 by sliding of the blood vessel 18 up the inclined portion and into the channel 36.

Embodiments of the improved surgical clamping device 10 can comprise an enlarged channel wall 46 to aid retention of the blood vessel 18 in the channel 36. The enlarged channel wall 46 helps prevent the blood vessel 18 sliding out of the channel 36 after movement of the blood vessel 18 up the inclined portion 44 and into the channel 36.

FIG. 5C shows a further embodiment of the improved surgical clamping device 10, wherein the elongate clamping member 14 comprises the inclined portion 44, channel 36 and enlarged channel wall 46 as described in relation to the previous embodiment shown in FIG. 5B. In the embodiment shown in FIG. 5C, the elongate clamping member 16 comprises a projection 48 aligned with the channel 36 in the other elongate clamping member 14 to securely clamp the blood vessel 18 in position when the separation between the elongate clamping members 14, 16 is reduced. Elongate clamping member 16 also comprises recess 42 for receiving aligned enlarged channel wall 46. This arrangement prevents the elongate clamping members 14, 16 being closed with too much pressure, thus preventing trauma to the blood vessel 18 being clamped.

In the embodiment shown in FIG. 5C, a magnifying device 50, such as a lens, can be provided on clamping member 16 above the projection 48 to aid location of the vein or artery 18 to be clamped. Where a magnifying device 50 is provided on clamping member 16, projection 48 is transparent. In some embodiments, magnifying device 50 can be mounted to body 12.

In the embodiment shown in FIG. 5C, the output device 32, such as an LCD screen or seven segment display, can be mounted to, or otherwise integrated with, elongate clamping member 16 to provide a reading of the blood flow in the constricted vein or artery 18 or to confirm that there is no blood flow when the vein or artery 18 is occluded.

For some of the aforementioned embodiments, the elongate clamping members 14, 16 may be integrally formed with the body 12 to simplify manufacturing and minimize cost of production. However, for some embodiments the elongate clamping members 14, 16 are manufactured separately. For example, in the embodiment shown in FIG. 1, the elongate clamping members 14, 16 can be molded from plastics material whereas the body 12 and the internal components thereof, such as the controller and microchip can be fabricated using MEMS techniques well known in the art, such as deposition, patterning, etching and micromachining.

For some of the aforementioned embodiments, the elongate clamping members 14, 16 are detachable from the body 12. In such embodiments, the elongate clamping members may be disposable and hence intended for single use or may be reusable. In at least some embodiments, the body 12 is reusable and may be sealed sufficiently that the body can be sterilized after each use.

Hence, another aspect of the present invention is a surgical clamping kit comprising a reusable body 12 and a plurality of interchangeable elongate clamping members 14, 16. The elongate clamping members required for a particular procedure and/or for a particular patient and/or vein/artery can be selected and coupled to the body 12. The elongate clamping members can be provided in pairs and disposed of after a single use. Alternatively, in embodiments where only one of the elongate clamping members moves, the elongate clamping members can be provided singly and disposed of after a single use. In these examples, one of the elongate clamping members is permanently coupled to the body and can be reused along with the body after sterilization.

In the aforementioned embodiments, a length of the elongate clamping members 14, 16 may be selectable from a plurality of predetermined lengths. The predetermined length selected can depend on the vein/artery to be clamped and/or the procedure for which the improved surgical clamping device 10 is intended. According to some embodiments, three different lengths may be provided. However, these embodiments of the present invention are not limited to the particular number.

The improved surgical clamping device 10 can be made from any material or combination of materials suitable for surgical use. For example, where the body 12 and/or elongate clamping members 14, 16 are made from plastics materials, biocompatible polymers can be used, such as, but not limited to polycarbonates, polyesters, polyamides, homopolymer polypropylene and acetal copolymer. Where the body 12 and/or elongate clamping members 14, 16 are made from metals, stainless steel, aluminium, titanium, titanium alloys, nickel alloys or shape memory alloys can be used. Ceramics, rubber, glass, carbon fibre, composites and/or other known materials can also be used.

Further details of embodiments of the present invention will now be described with reference to FIGS. 6A-13F.

Figure 6A:
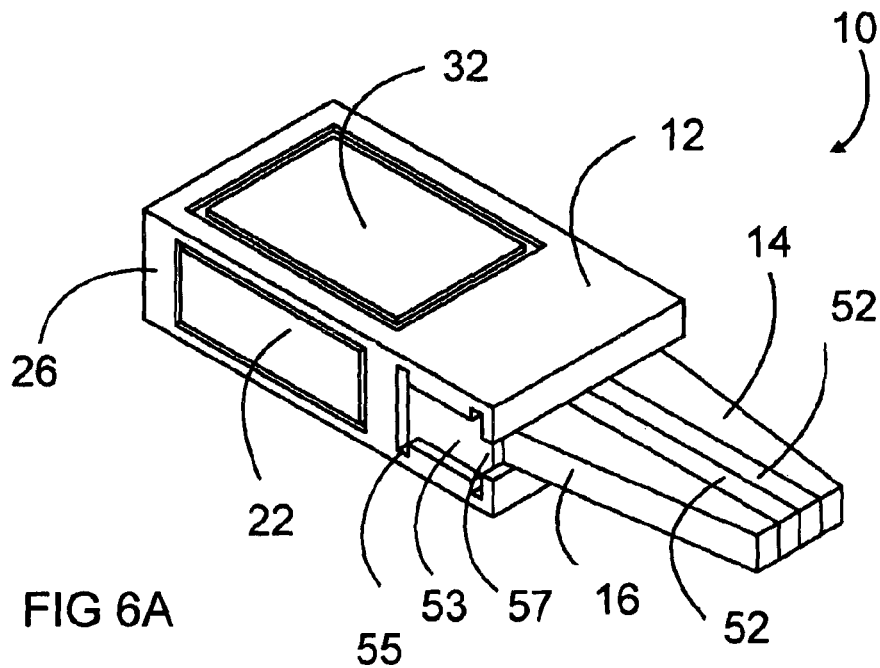
FIG. 6A is an isometric view of a surgical clamping device according to an embodiment of the present invention.

Referring to FIG. 6A, smart surgical clamping device 10 comprises body 12 and a pair of elongate clamping members 14, 16 extending from the body for clamping a blood vessel 18, such as an artery, vein, or capillary therebetween. Clamping members 14, 16 comprise, or are coupled to, a respective mount 53 that moves along tracks 55 to facilitate movement of the elongate clamping members 14, 16. Body 12 can comprise one or more apertures 57 to allow for movement of mounts 53 and clamping members 14, 16 at least partially outside of body 12, as shown in FIG. 6C. In this embodiment, elongate clamping members 14, 16 have a tapered shape and comprise soft cushioning layers 52 to help minimise trauma to the blood vessel.

Output device 32 in the form of a graphic micro LED display shows system messages, operation instructions, sensory data, battery information, diagnostic data, self-test data, and other relevant information for effective user interaction. The micro LED display is connected to an embedded microcomputer as a digital output. The operation of the micro LED display is programmed in computer implemented code run on the embedded microcomputer.

Actuator 22 in the form of a pushbutton is mounted on first side wall 26 of the body 12 to receive user commands including opening and closing of elongate clamping members 14, 16 and emergency stopping of the clamping members 14, 16 during opening or closing of the clamping members. The pushbutton is connected to the embedded microcomputer as a binary input. The function of the pushbutton is programmed in the computer implemented code run on the embedded microcomputer. FIG. 6A shows the elongate clamping members 14, 16 in a fully closed position.

Figure 6B:
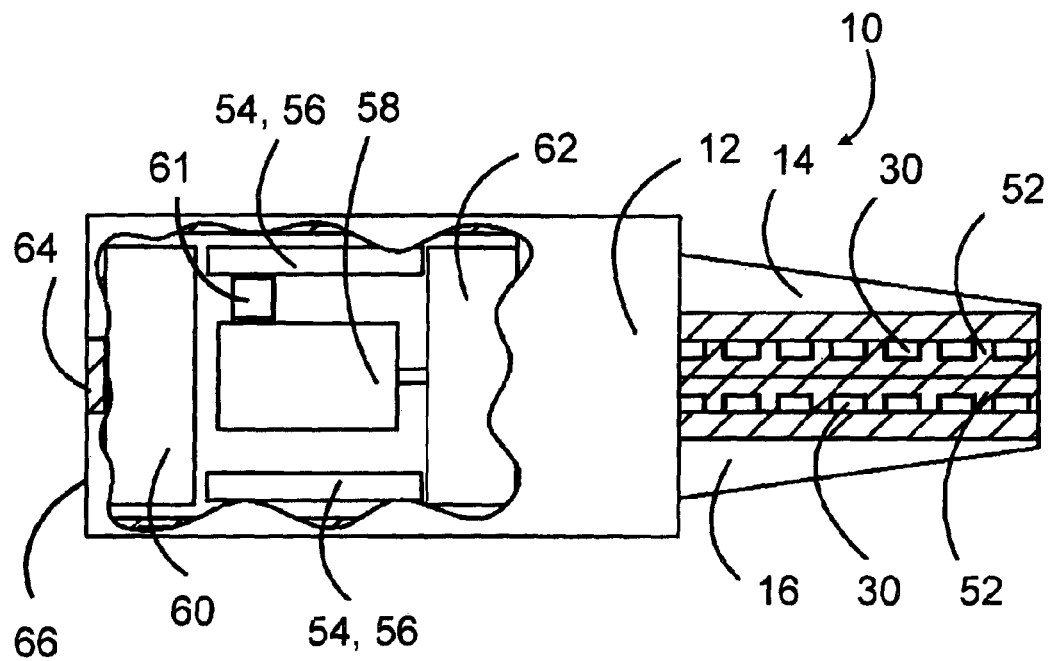
FIG. 6B is a partially cut-away top view of the surgical clamping device of FIG. 6A showing internal components of the device.
Figure 6C:
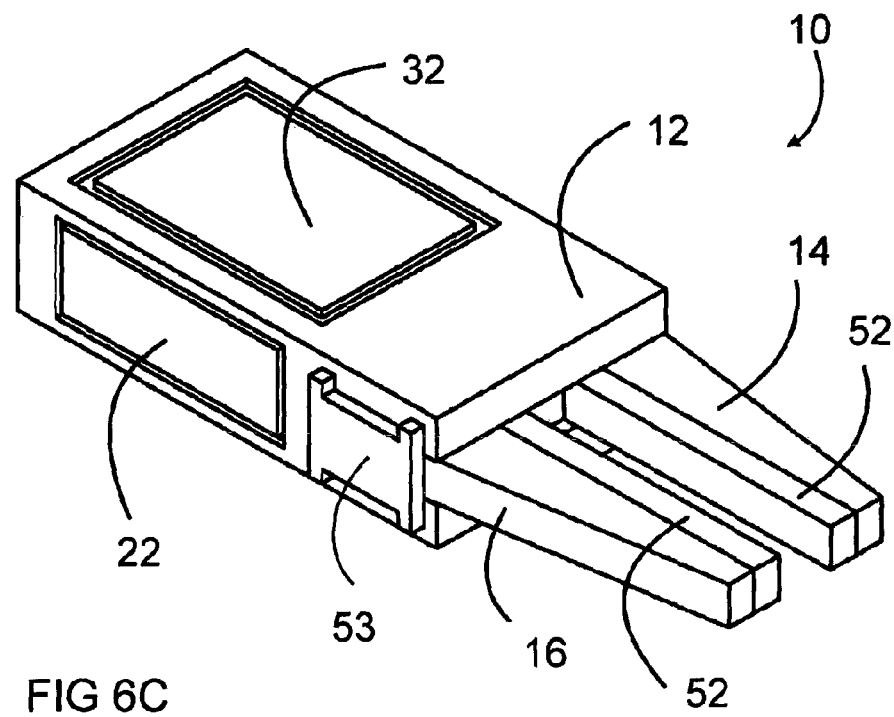
FIG. 6C is an isometric view of the surgical clamping device of FIG. 6A showing the elongate members in an open position.

Referring to FIG. 6B, body 12 houses all internal components of the device 10 and supports elongate clamping members 14, 16 comprising soft cushioning layers 52. Embedded microcomputer 54 involves a low-power microcontroller, on-board memory and digital and analogue input/output ports. Body 12 can also house a buzzer and/or loudspeaker 61 in the form of a micro speaker for sounding an alarm or indicator as required during use of the clamping device 10. Microcomputer 54 executes the computer implemented system code in real-time and controls the operation of the clamping device 10. Computer implemented system code can include code for data acquisition, monitoring, control, communication, data logging, self-test, and user interface modules. According to one embodiment, a circuit for the microcomputer 54 is assembled on two small multilayer printed circuit boards 56 mounted within the body 12 of the clamping device 10.

A micro-motor 58 is situated substantially centrally within the body 12, which is coupled to and powered by a power supply in the form of battery 60. A micro-gearbox 62 is coupled to the micro-motor 58 to actuate elongate clamping members 14, 16. Micro-gearbox 62 enables controlled transmission of power from the micro-motor 58 to the elongate clamping members 14, 16 by converting rotational power of the micro-motor 58 to linear motion of the elongate clamping members 14, 16. Micro-gearbox 62 also converts the rotational speed of the micro-motor 58 to an appropriate linear speed and power of the elongate clamping members 14, 16. Additionally, when the elongate clamping members 14, 16 are in the desired position, micro-gearbox 62 acts as a brake, thus preventing further motion of the elongate clamping members 14, 16. This enables the micro-motor 58 to go into a sleep mode thus eliminating the requirement to maintain power to the micro-motor 58, which results in a reduction of battery power use.

A blood flow sensor 30 in the form of a blood flow sensor array is mounted at the interface of the elongate clamping members 14, 16 and respective cushioning layers 52 for continuous monitoring of the blood flow rate. Irrespective of the location of the blood vessel 18 in between the clamping members 14, 16, the sensor array 30 monitors the blood flow passing through the vessel 18 and transmits the information to the microcomputer 54 for monitoring, logging, and/or control actions.

Battery 60 can be in the form of a high-power button-cell lithium-ion battery, which powers the entire clamping device including the embedded microcomputer 54, blood flow sensor 30, and actuation of the clamping members 14, 16 including the micro-motor 58 and micro-gearbox 62. However, it will be appreciated that other types of power supply can be used.

FIG. 6C shows the elongate clamping members 14, 16 in a partially open position ready to receive a blood vessel. In this embodiment, mounts 53 protrude through aperture 57 in the body 12.

Figures 6D, 6E:
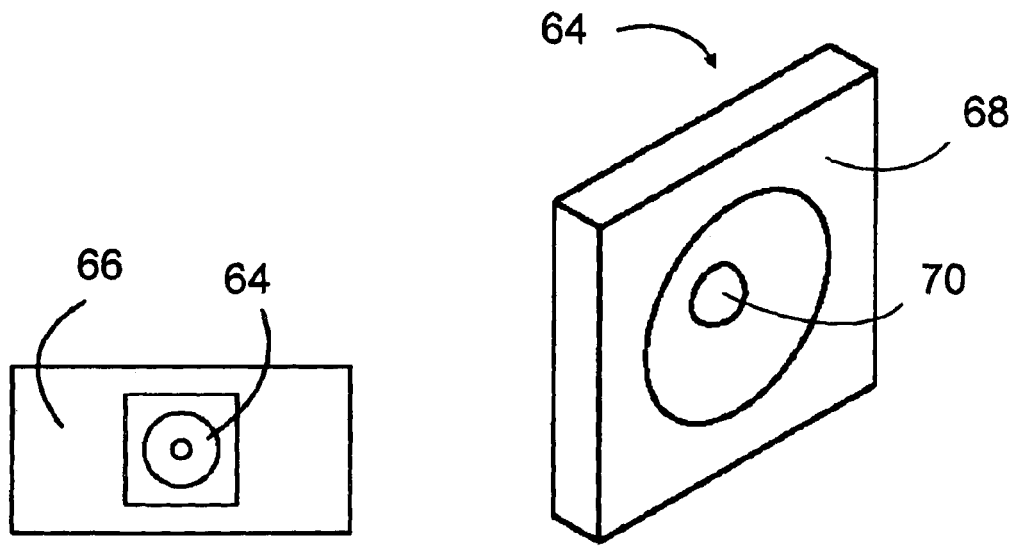
FIG. 6D is an end view of the device of FIG. 6A.
FIG. 6E is an enlarged isometric view of a mounting member of the device for connection to a surgical clamping applicator.

With reference to FIGS. 6D and 6E, a mounting member 64 is coupled to an end wall 66 of body 12 of the clamping device 10 to enable the clamping device to be attached to an applicator, which will be described in further detail herein. The mounting member 64 enables the exchange of control and data messages in serial form and enables the clamping device 10 to be fully operated through the applicator. The mounting member 64 comprises a mounting platform 68 and signal and ground electrodes 70.

Figure 7:
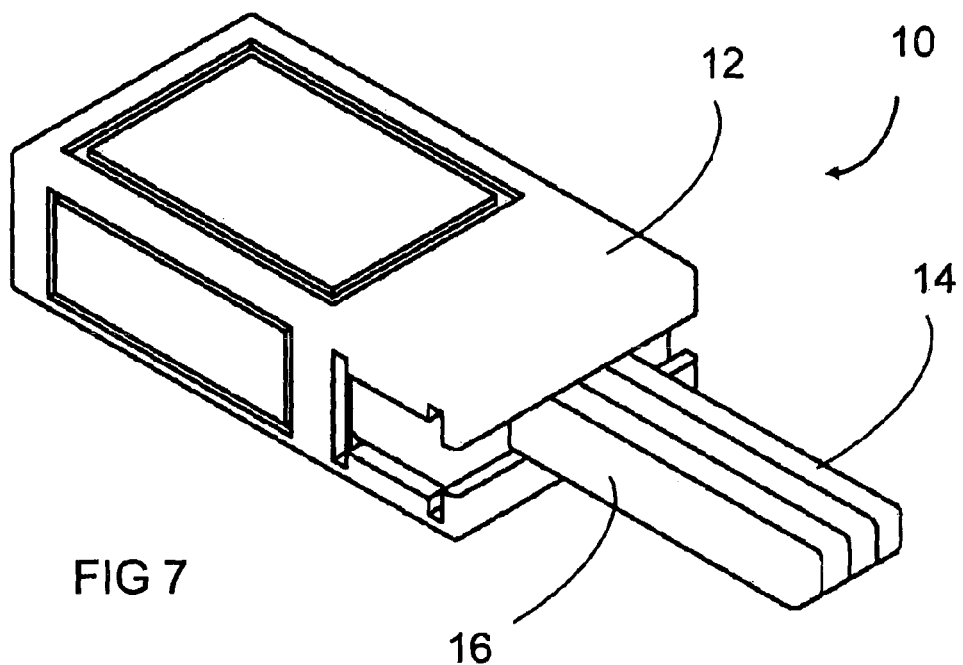
FIG. 7 is an isometric view a surgical clamping device according to another embodiment of the present invention showing the elongate members in a fully closed position.

FIG. 7 shows another embodiment of the surgical clamping device 10 comprising substantially rectangular-shaped elongate clamping members 14, 16 rather than the tapered shape shown in FIGS. 6A-6C. Both the clamping members 14, 16 and the edges of the body 12 have smoothed rounded edges.

Figure 8:
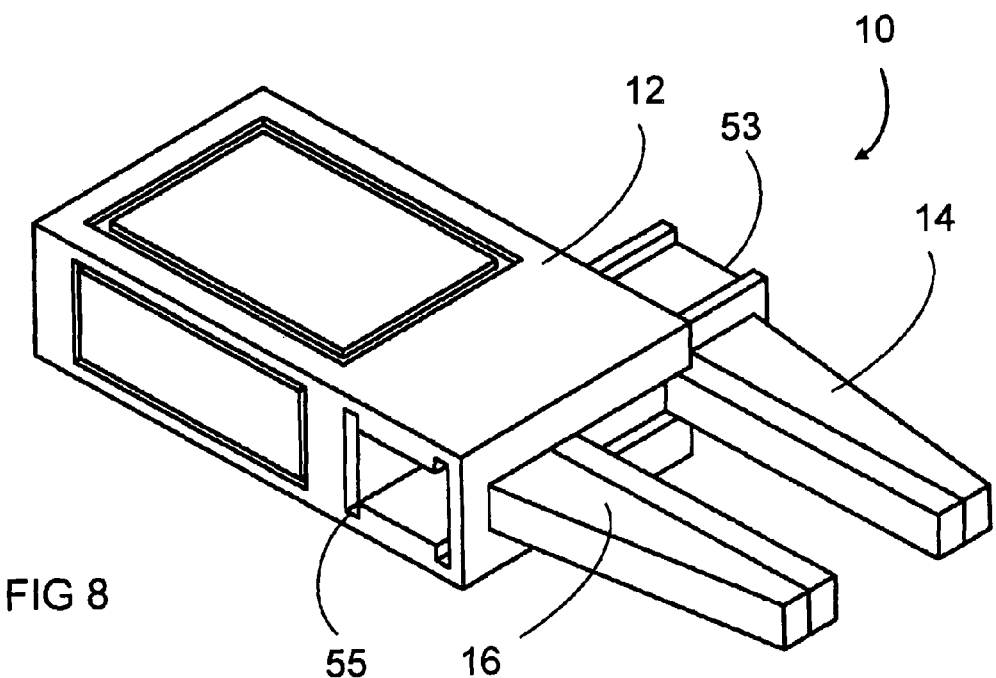
FIG. 8 is an isometric view a surgical clamping device according to a yet further embodiment of the present invention.

In the embodiment shown in FIG. 8, surgical clamping device 10 comprises one fixed elongate clamping member 16 and one movable elongate clamping member 14. Clamping member 14 comprises mount 53, which moves along tracks 55, whereas clamping member 16 does not comprise a mount and can be fixed to the body 12.

Figure 9A:
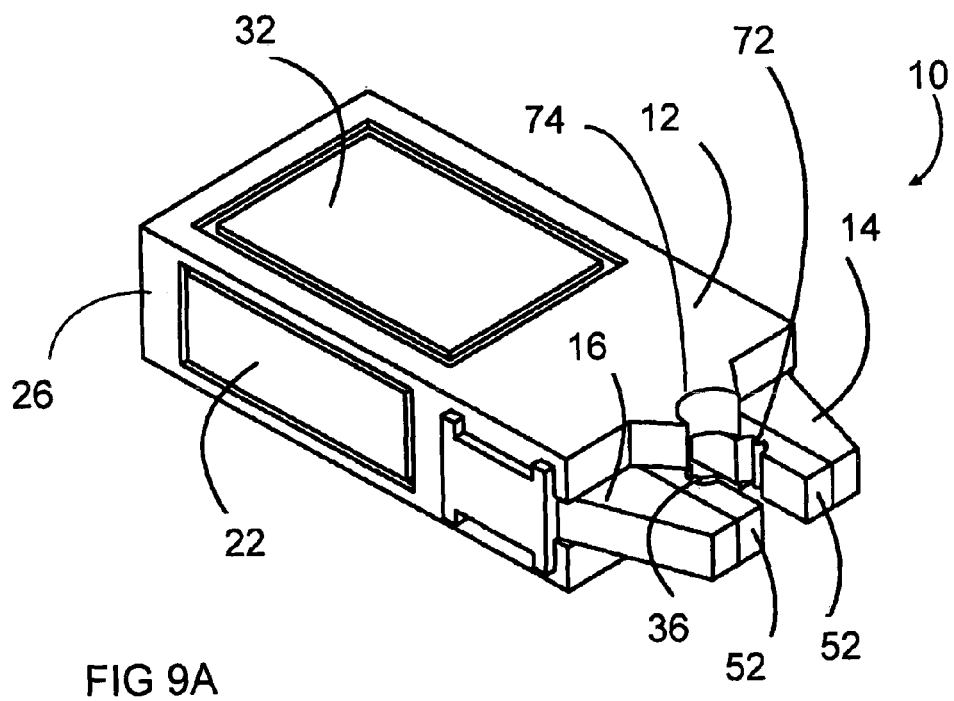
FIG. 9A is an isometric view a surgical clamping device according to another embodiment of the present invention.
Figure 9B:
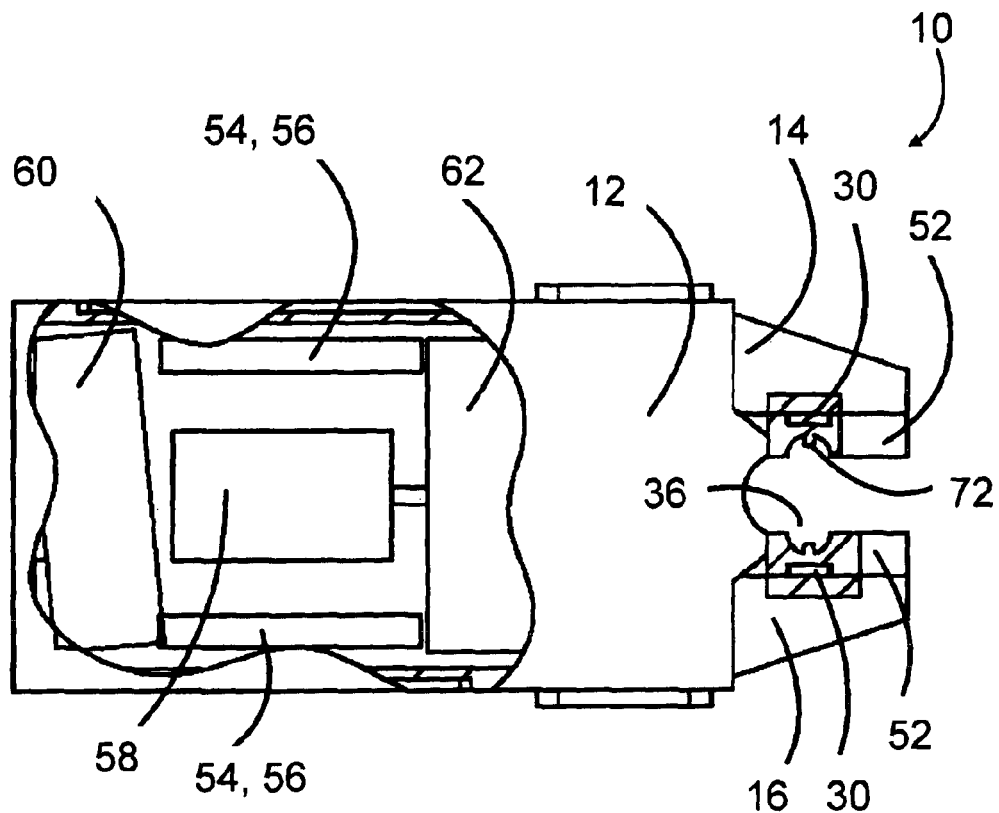
FIG. 9B is a top view of the surgical clamping device of FIG. 9A showing internal components of the device.

With reference to the embodiment shown in FIGS. 9A and 9B, surgical clamping device 10 comprises shorter clamping members 14, 16 compared with previous embodiments described herein. In this embodiment, clamping members 14, 16 have a tapered shape and comprise soft cushioning layers 52 incorporating a channel 36 for holding the blood vessel 18. Channels 36 comprise a central ridge 72, which aids retention of the blood vessel 18 in the channel 36 since the cross sectional shape of the blood vessel is not necessarily perfectly circular. A single blood flow sensor 30 is located adjacent the channel 36 for monitoring the blood flow rate. The user places the channels 36 of the elongate clamping members around the blood vessel and activates closure of the elongate clamping members 14, 16 by pressing actuator 22. Blood flow sensor 30 detects when blood flow in the blood vessel is occluded and halts closure of the elongate clamping members 14, 16. This embodiment comprises arcuate platform 74 in body 12 to further aid positioning of the surgical clamping device 10. A user pushes the clamping device 10 forward until a resistance is sensed by a suitable sensor indicating that the blood vessel is located in the arcuate platform 74.

Figure 9C:
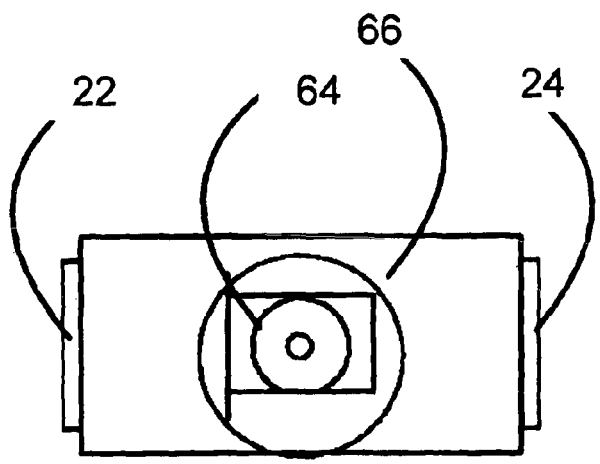
FIG. 9C is an end view of the surgical clamping device of FIG. 9A showing a mounting member of the device for connection to a surgical clamping applicator.

FIG. 9C shows mounting member 64 coupled to end wall 66 of body 12 of the clamping device 10 to enable the clamping device to be attached to an applicator. FIG. 9C also shows actuators 22, 24 protruding from body 12.

Whilst some of the embodiments are shown comprising actuators 22, 24 on side walls 26 and output device 32 on a substantially perpendicular top wall of the device 10, it will be appreciated that other configurations are envisaged, such as the output device 32 being provided on one of the side wall 26 and one of the actuators 22, 24 provided on the top wall of the device 10.

In use, a user holds the body 12 of surgical clamping device 10 using two fingers placed on top of actuators 22, 24. In some embodiments, pressing one of the actuators fully opens elongate clamping members 14, 16. Device 10 is then brought into the vicinity of the blood vessel to be clamped and the user places the spaced apart clamping members 14, 16 either side of the vessel. Pressing one of the actuators 22, 24 commences closure of the elongate clamping members 14, 16. The user can stop closing of the clamping members 14, 16 at any time by pressing one of the actuators 22, 24. Whilst the clamping members 14, 16 are closing, blood flow sensor 30 is continuously monitored by the microcomputer. Once a predetermined blood flow rate is sensed, the microcomputer stops closure of the elongate clamping members 14, 16, sounds the alarm or buzzer, displays a message on the display 32, and ceases supply of power to the micromotor 58 to conserve power in battery 60. Micro-gearbox 62 ensures that the clamping members 14, 16 are locked in position and cannot move. Upon hearing of the alarm and/or viewing the message on the display 32, the user releases the clamping device 10 whilst connected to the blood vessel 18.

The microcomputer continues to monitor the blood flow sensor 30, the actuators 22, 24 and the communication port in real-time. If the blood flow rate increased or decreased beyond the desired rate at any given time during the procedure/operation, the microcomputer causes the micro-motor 58 to adjust separation of the clamping members 14, 16 to maintain the desired flow rate. This adjustment is carried out in a few milliseconds.

At the conclusion of the procedure/operation, the user presses one of the actuators 22, 24 and the microcomputer opens the clamping members 14, 16 using micro-motor 58 to enable detachment of the device 10 from the blood vessel.

The surgical clamping device 10 exchanges control and data signals through wired and/or wireless serial communications. The device 10 can communicate with an applicator as described hereinafter and/or an external computer through the wired and/or wireless communication means.

Figure 10A:
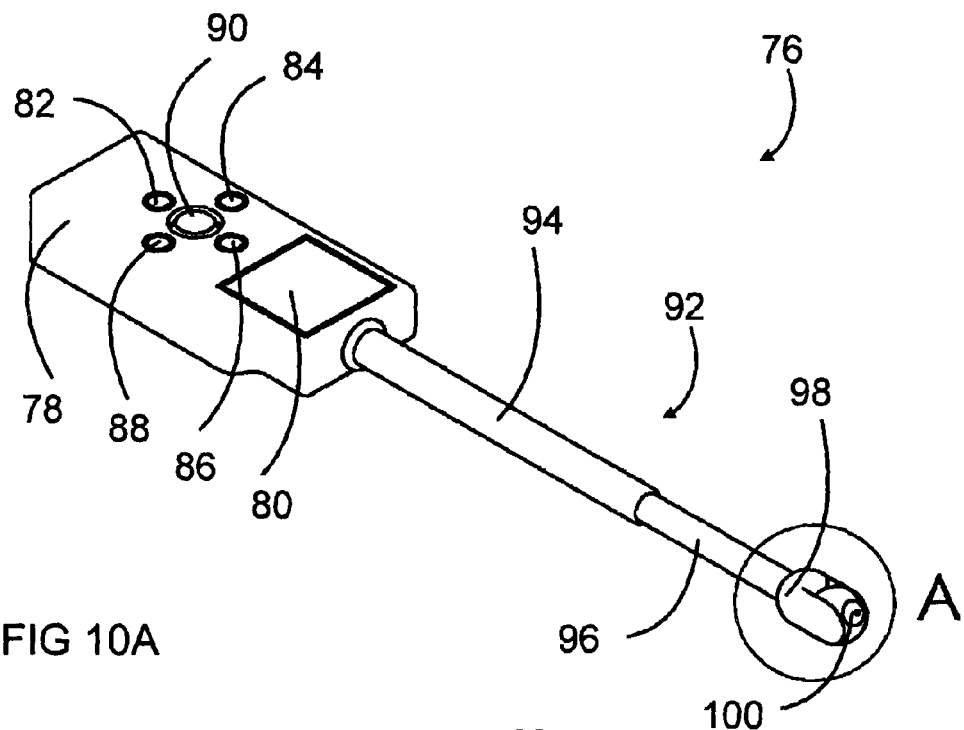
FIG. 10A is an isometric view an surgical clamping applicator according to another embodiment of the present invention showing an arm of the applicator in an extended position.
Figure 10B:
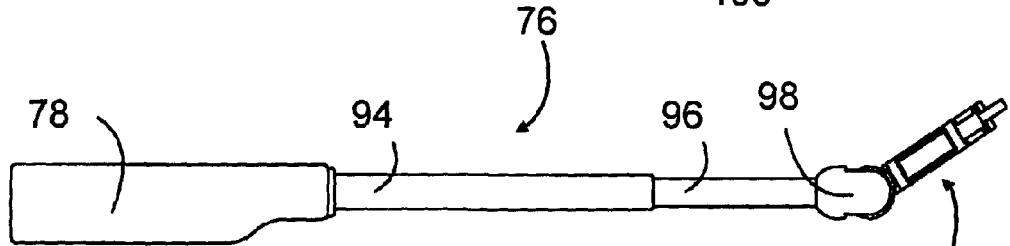
FIG. 10B is a side view of the surgical clamping applicator of FIG. 10A showing amounted surgical clamping device at an angle in vertical plane.
Figure 10C:
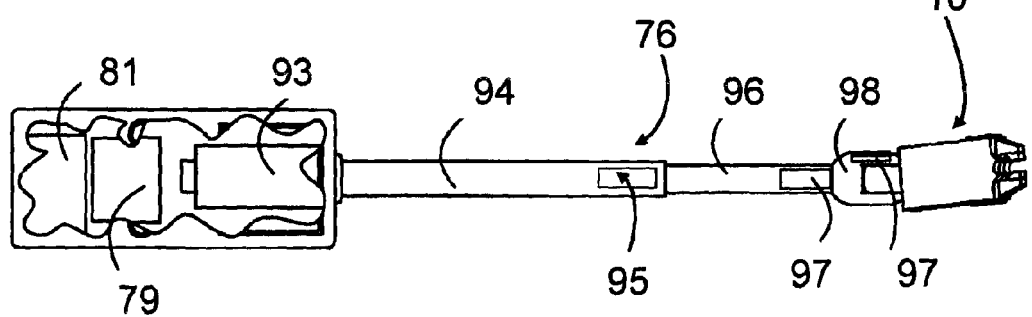
FIG. 10C is a partially cut-away top view of the surgical clamping applicator of FIG. 10A showing a mounted surgical clamping device at an angle in vertical plane.
Figure 10D:
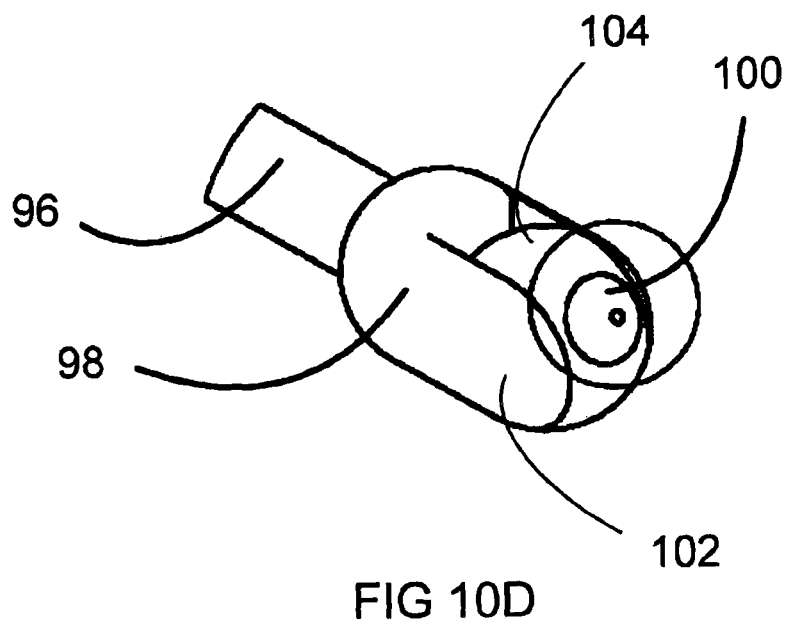
FIG. 10D is an enlarged isometric view of region A of FIG. 5A showing a head assembly of the applicator for connection to and positioning of a surgical clamping device.

Referring now to FIGS. 10A and 10C, according to another aspect of the present invention, a tool in the form of an applicator 76 is provided for use with the surgical clamping device 10. Applicator 76 comprises a body 78 which forms a handle for holding by a user. Body 78 contains an embedded microcomputer 79 comprising a low-power microcontroller, on-board memory and digital and analogue input/output ports, similar to such features described above in relation to the surgical clamping device 10 with reference to FIG. 6B. The microcomputer 79 of applicator 76 executes computer implemented code stored in the memory and controls operation of the applicator 76. The microcomputer circuit is assembled onto two small multilayer printed circuit boards mounted within the body 78 of the applicator and is powered by an internal battery 81.

Applicator 76 comprises an output device in the form of a graphic micro LED display 80 coupled to be in communication with the microcomputer of the applicator 76 to display system messages, operation instructions, sensory data, battery information, diagnostic data, and other relevant information for effective user interaction. Applicator 76 comprises input devices in the form of four push buttons 82, 84, 86, 88 and a directional controller 90, such as a joystick or roller ball, which are coupled to be in communication with the microcomputer of the applicator 76 to control distal extension and retraction of telescopic arm 92 of the applicator 76 as well as positioning control of a surgical clamping member 10 attached to a distal end of arm 92, as shown in FIGS. 10B and 10C.

Arm 92 comprises a cylindrical sleeve member 94, a proximal end of which is attached to body 78. Arm 92 also comprises an elongation member 96, which is housed within cylindrical sleeve member 94 in a retracted state. FIG. 10A shows arm 92 with elongation member 96 in an extended state. Applicator 76 comprises a pan tilt head 98 coupled to a distal end of elongation member 96. Pan tilt head 98 comprises an interface 100 for coupling surgical clamping device 10 to the pan tilt head 98 via mounting member 64 of the clamping device 10 and thus to the distal end of arm 92, as shown in FIGS. 10B and 10C.

Applicator 76 comprises a linear actuator 93 housed in body 78 and/or in cylindrical sleeve member 94 which controls the elongation of member 96. Linear actuation can be achieved via any known mechanism that enables linear movement of member 96 relative to sleeve member 94. As shown in FIG. 10A, the elongation member 96 can slide freely in and out of the sleeve member 94.

As shown in FIG. 10C, a locking mechanism 95 is incorporated in cylindrical sleeve member 94 to prevent elongation member 96 from sliding out of the sleeve member 94 completely. In some embodiments, the maximum extension of elongation member 96 is half of the total length of cylindrical sleeve member 94. The length of the cylindrical sleeve member 94 and elongation member 96 can be selectable from a plurality of predetermined lengths.

One or more micro-motors 97 are included in pan tilt head 98 and/or elongation member 96 to control the orientation and position of the surgical clamping device 10 attached to the head 98. With additional reference to FIG. 10D, pan tilt head 98 comprises a frame 102 supporting a ball member 104, which can pan and tilt relative to the frame 102, as illustrated by FIG. 10B, which shows the surgical clamping device 10 attached to ball member 104 inclined to the vertical, and by FIG. 10C, which illustrates the surgical clamping device 10 inclined to the vertical and angled to the left relative to a longitudinal axis of the applicator 76. The movement of the pan tilt head 98 is controlled via software stored in memory executed by the microcomputer 79 of the applicator 76 in response to inputs by the user via push buttons 82, 84, 86, 88 and/or directional controller 90. The pan tilt head 98 allows the surgical clamping device 10 attached thereto to be manoeuvred at different angles and positions, as shown in FIGS. 10B and 10C. Both the elongation member 96 and the pan tilt head 98 enable the device 10 to be operated at a distance in range of different locations within the animal or human body.

Figure 10E:
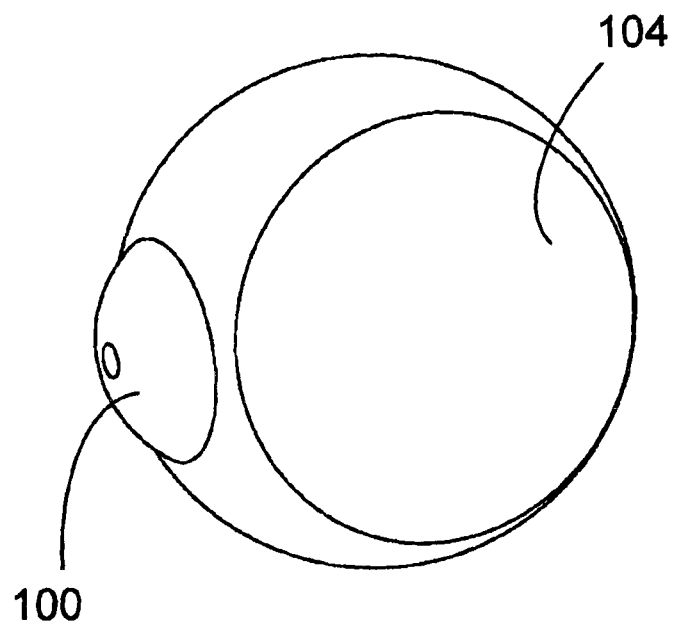
FIG. 10E is an isometric view of a mounting member of the head assembly of the applicator shown in FIG. 10D.
Figure 10F:
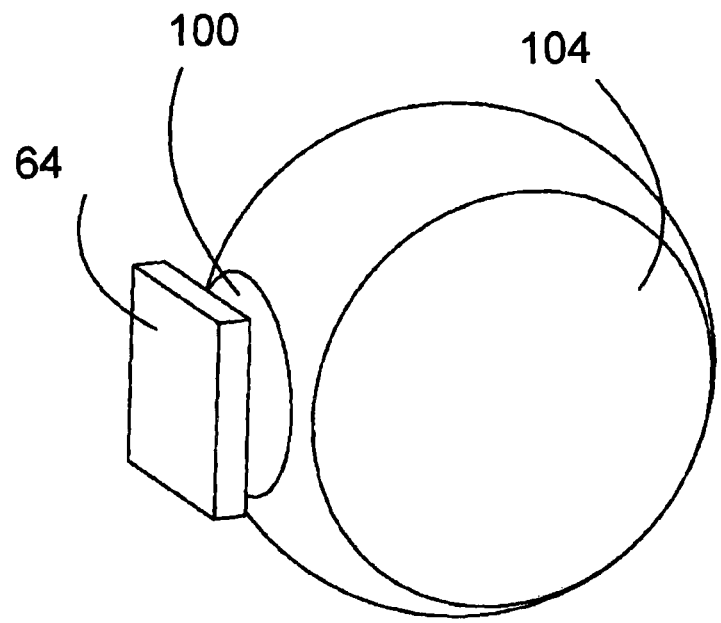
FIG. 10F is an isometric view of the mounting member shown in FIG. 10E coupled to the mounting member for the surgical clamping device shown in FIG. 6E.
Figure 10G:
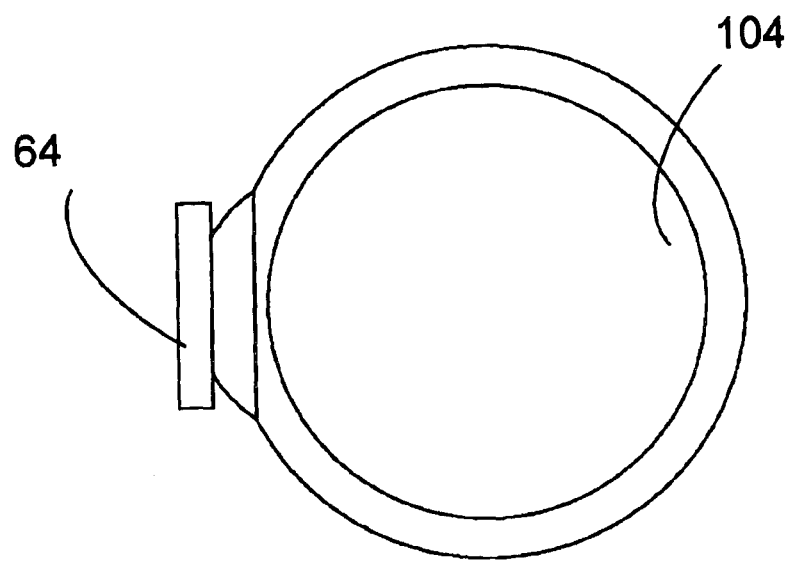
FIG. 10G is a side view of the arrangement shown in FIG. 10F.

Interface 100 has an electromagnetic system which is controlled by the microcomputer. Interface 100 can be magnetized and de-magnetized using one or more of the push buttons 82, 84, 86, 88 on the body 78 of the applicator 76. When the user wants to connect the applicator 76 to a surgical clamp 10, one of the push buttons 82, 84, 86, 88 is depressed to magnetize interface 100 causing the interface 100 to be attracted towards mounting member 64 of surgical clamping device 10. Referring to FIG. 10E, during the magnetization phase, the rounded shape of interface 100 has a complementary shape to mounting member 64 thus enabling the applicator to interlock with mounting member 64 of the surgical clamping device 10, as shown in FIGS. 10F and 10G. After adjusting the position and orientation of the clamping device 10 via the directional controller 90, the user disengages the surgical clamping device 10 from the applicator 76 by depressing one of the push buttons 82, 84, 86, 88 to disable generation of the electromagnetic signal.

Applicator 76 can be made from any material or combination of materials suitable for surgical applications. For example, body 78, cylindrical sleeve member 94, elongation member 96 and pan tilt head 98 can be made of plastics materials such as, but not limited to polycarbonates, polyesters, polyamides, homopolymer propylene and acetal copolymer or other known materials. Interface 100 can be made of any material with magnetic properties.

Figure 11:
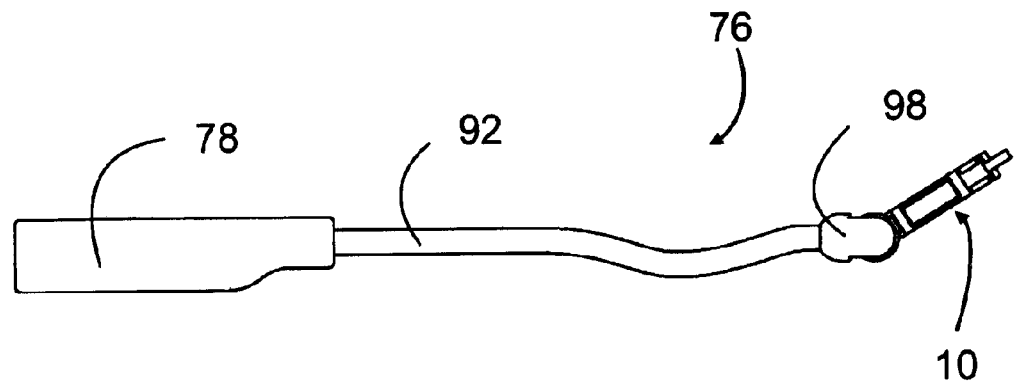
FIG. 11 is a side view of a surgical clamping applicator comprising a flexible arm for varying configurations.

With reference to FIG. 11, another embodiment of the applicator 76 comprises an arm 92 which is flexible enabling the user to shape the arm 92 to the desired configuration for improved ease of access for many different applications. In this embodiment, arm 92 can be constructed from any suitable material, or combination of materials, that allow the shape of the arm to be changed and the changed shape to be maintained for the application.

In use, a user manually attaches surgical clamping device 10 to the applicator 76 via mounting member 64 on end wall 66 of the clamping device body 12 and interface 100 of pan/tilt head 98 the applicator 76. Attachment is detected automatically through exchange of signals between the clamping device 10 and the applicator 76 causing activation of the electromagnetic system to secure the clamping device 10 to the applicator 76. The electromagnetic system can be also activated and deactivated by the user by pressing one of the push buttons 82, 84, 86, 88 on the applicator body 78 at any given time.

Once the electromagnetic system is activated, control of the clamping device 10 is managed through the push buttons 82, 84, 86, 88 and the direction controller 90 of the applicator 76. Information from the blood flow sensor array 30 is relayed to the applicator 76 from the clamping device 10 in real-time through the serial communication ports.

The clamping device 10 is brought into the vicinity of the blood vessel via the applicator 76 and manoeuvred via the direction controller 90 until the elongate clamping members 14, 16 are around the vessel. Closure of the clamping members 14, 16 is controlled by push buttons 82, 84, 86, 88 on the applicator 76. Blood flow sensor 30 in the device 10 monitors blood flow during closure as described above. Microcomputer 79 of the applicator 76 stops closure of the clamping members 14, 16 once a predetermined blood flow rate is sensed, sounds an alarm in the applicator 76, displays a message on the display 80 of the applicator 76, and ceases power to the micro-motor 68 in clamping device 10.

Upon hearing the alarm and/or viewing the message on display 80, the user deactivates the electromagnetic system of the applicator 76 whilst the clamping device 10 is connected to the blood vessel. The microcomputer 54 of the clamping device 10 resumes control and continues to monitor the blood flow sensor 30.

If the blood flow rate increases or decreases beyond the desired rate at any given time during clamping, the microcomputer 54 adjusts the separation of the clamping members 14, 16 to maintain the desired flow rate as described above.

At the conclusion of the procedure/operation, the user positions the interface 100 of pan/tilt head 98 of the applicator 76 near the mounting member 64 of clamping device 10 and couples the clamping device to the applicator 76. The user presses one of push buttons 82, 84, 86, 88 on applicator 76 to open clamping members 14, 16 to detach the clamping device 10 from the vessel.

Figure 12A:
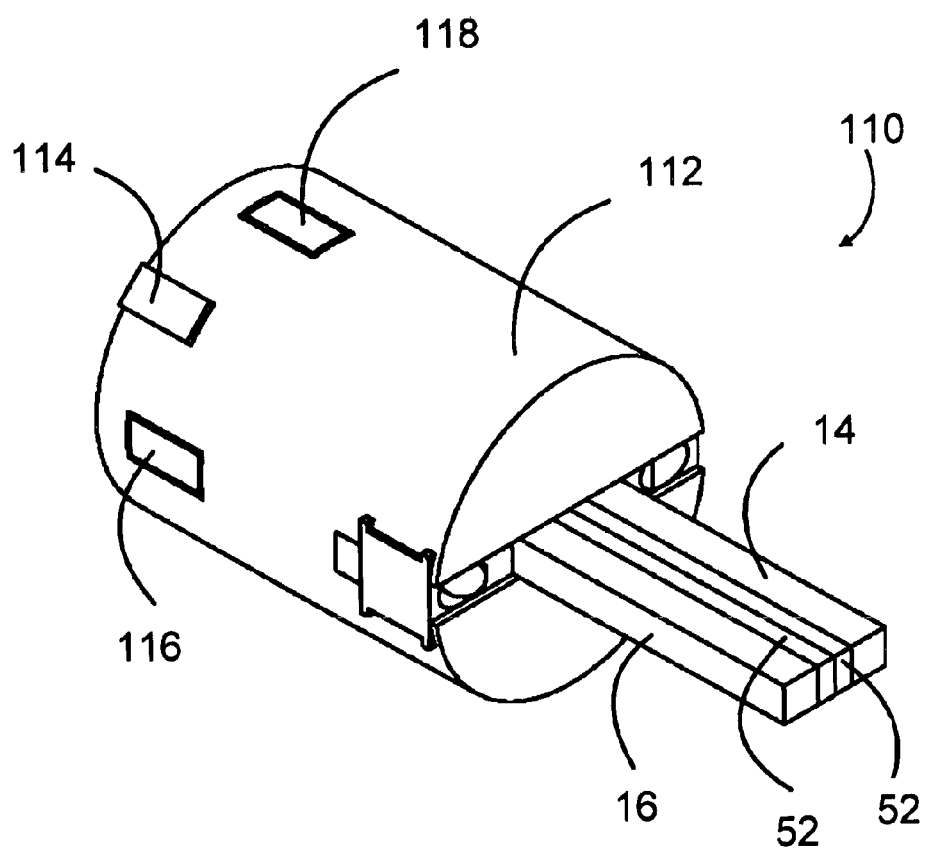
FIG. 12A is an isometric view of a surgical micro-clamping device according to another embodiment of the present invention.
Figure 12B:
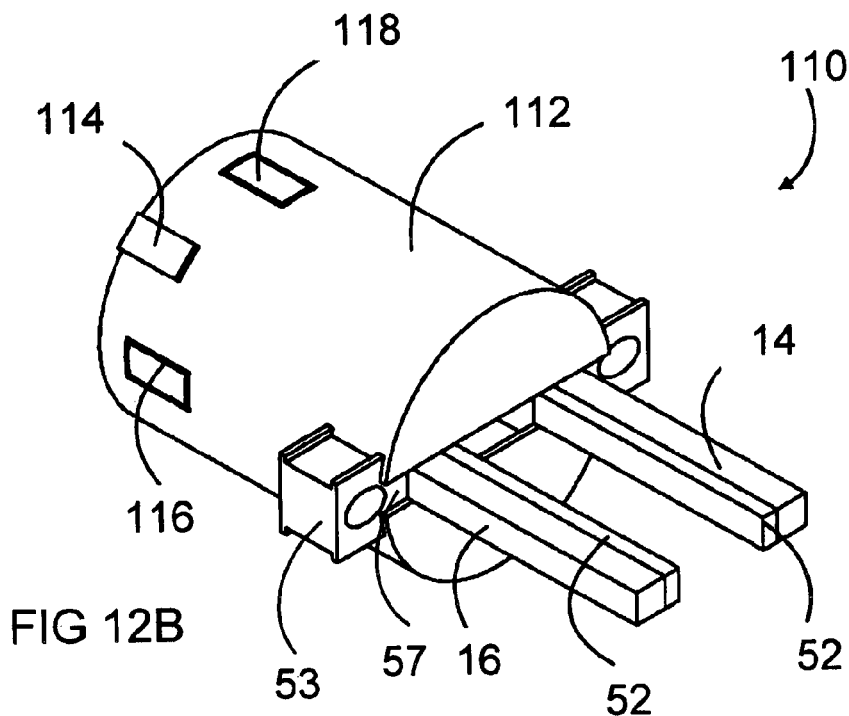
FIG. 12B is an isometric view of the device of FIG. 12A showing the elongate members in an open position.

Referring to FIGS. 12A and 12B, a smart surgical micro-clamping device 110 is shown comprising a substantially cylindrical body 112 and a pair of elongate clamping members 14, 16 extending from the body for clamping a capillary. Clamping members 14, 16 comprise soft cushioning layers 52 to help minimise trauma to the capillary. Body 112 comprises a mounting guide 114 and electrodes 116, 118 for coupling the micro-clamping device 110 physically and electrically to a micro-clamping applicator which will be described in further detail hereinafter. In one embodiment, micro-clamping device 110 comprises four electrodes, only two of which are visible in FIGS. 12A and 12B. Body 112 houses all internal components of the device 110 and supports the elongate clamping members 14, 16. FIG. 12A shows the clamping members 14, 16 in a closed position and FIG. 12B shows the clamping members 14, 16 in a partially open position. Clamping members 14, 16 comprise, or are coupled to, a respective mount 53 that moves along tracks 55 and through one or more apertures 57 in body 12 to facilitate movement of the elongate clamping members 14, 16.

Figure 12C:
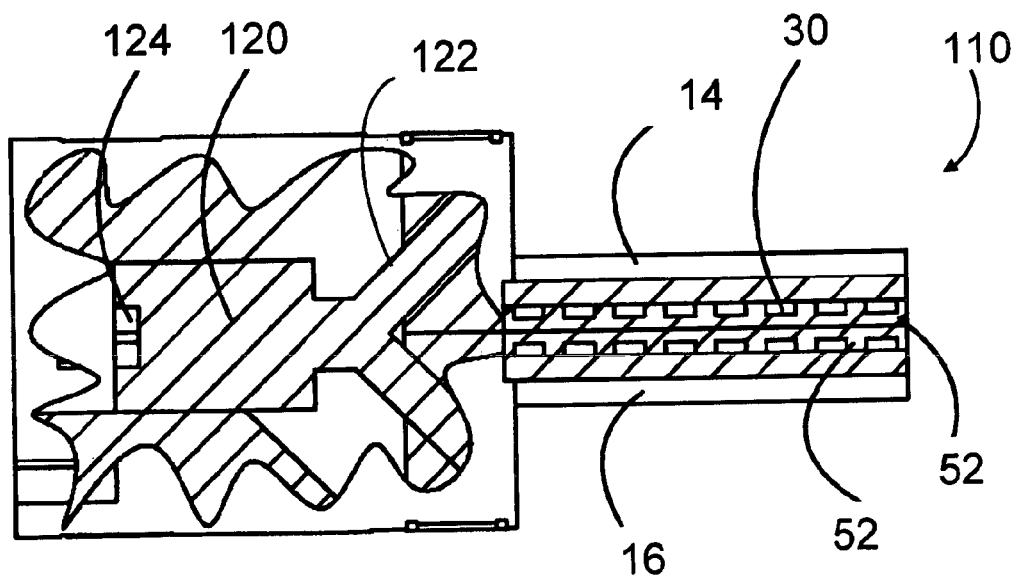
FIG. 12C is a schematic top view of the device of FIG. 12A showing internal components of the device.

With reference to FIG. 12C, surgical micro-clamping device 110 comprises an embedded blood flow sensor array 30, a linear micro-actuator 120, actuation arms 122 for moving elongate clamping members 14, 16 and a coupling member 124 to couple the micro-clamping device 110 to the micro-clamping applicator. Linear micro-actuator 120 actuates the clamping members 14, 16. In some embodiments, linear micro-actuator 120 comprises a cavity or hollow core with an internal thread and a threaded rod inside the cavity. The threaded rod comprises coupling member 124 at one end and actuation arms 122 at an opposite end.

Figure 12D:
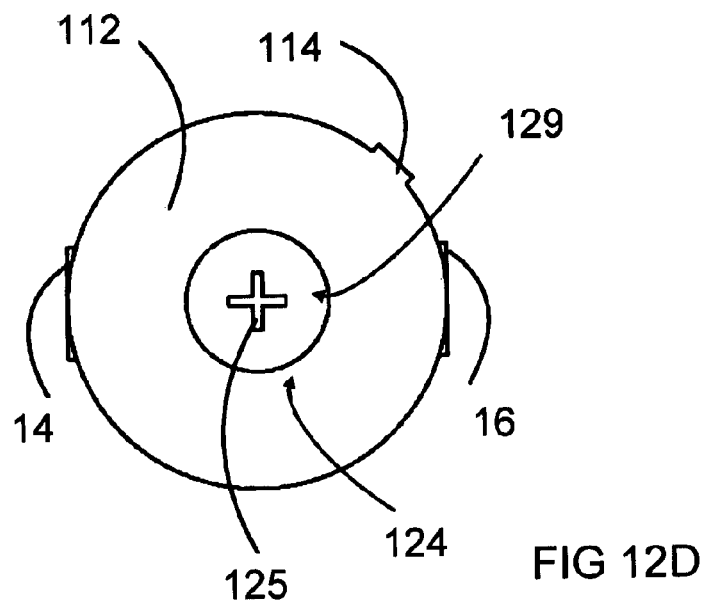
FIG. 12D is an end view of the device of FIG. 12A showing a mounting member of the device for connection to a surgical micro-clamping applicator.
Figure 13A:
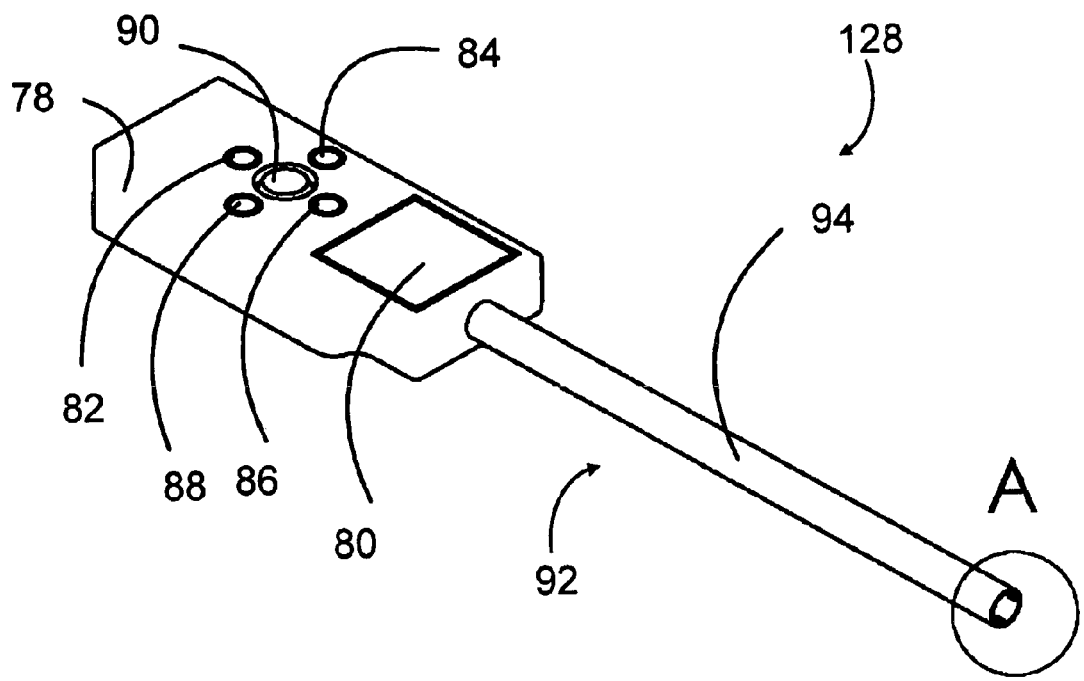
FIG. 13A is an isometric view an surgical micro-clamping applicator according to a further embodiment of the present invention.
Figure 13B:
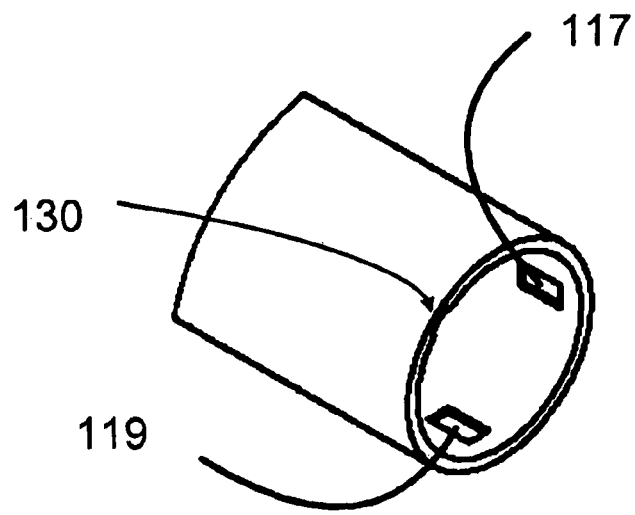
FIG. 13B is an enlarged isometric view of a cylindrical sleeve member of the applicator of FIG. 13A for connection to a surgical micro-clamping device.
Figure 13C:
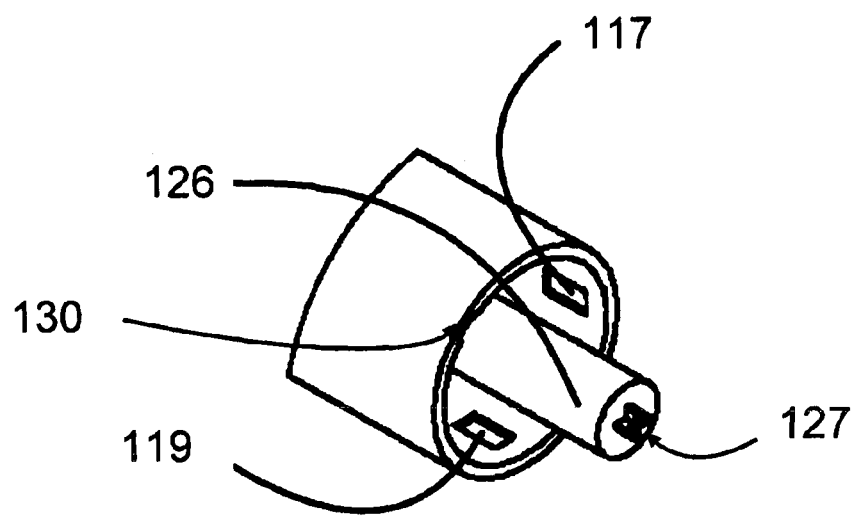
FIG. 13C shows the cylindrical sleeve member of FIG. 13B with a connecting rod of the applicator in an extended position.
Figure 13D:
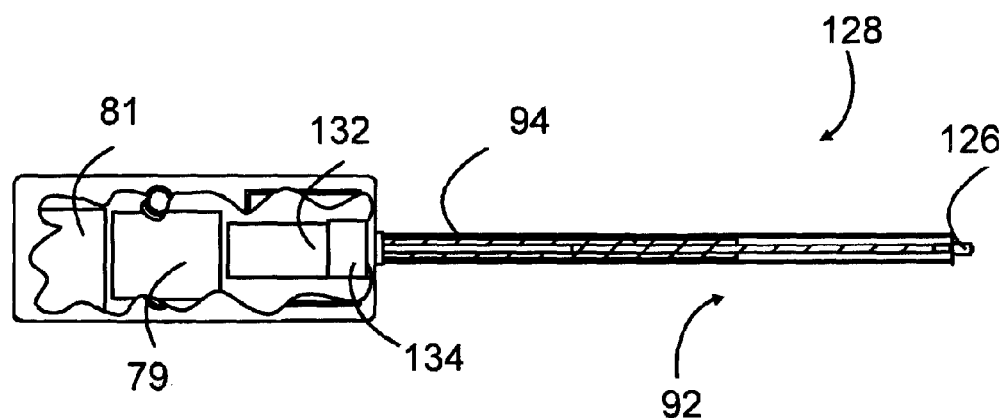
FIG. 13D is a partially cut-away top view of the applicator of FIG. 13A.
Figure 13E:
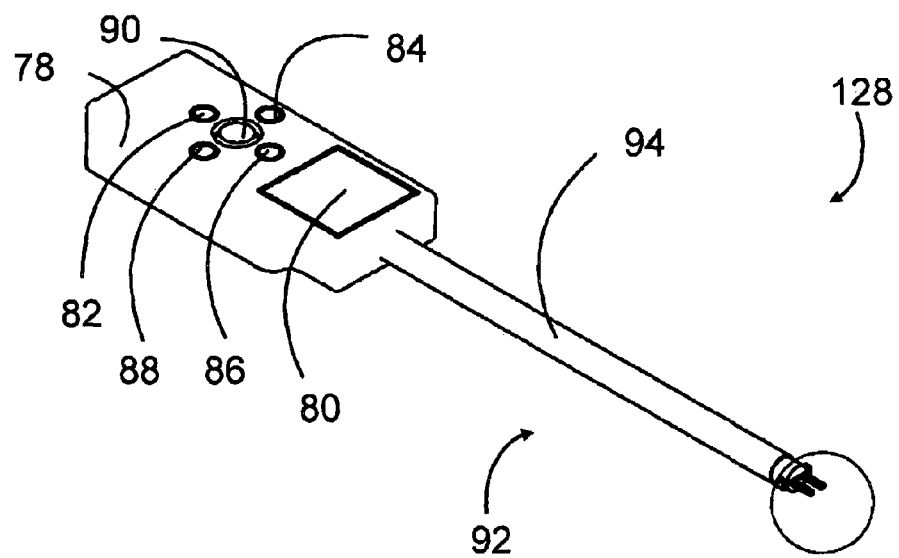
FIG. 13E is an isometric view of the applicator of FIG. 13A showing a surgical micro-clamping device mounted thereto.

In some embodiments, coupling member 124 comprises a cross-shaped recess 125, as shown in FIG. 12D. However, other shapes of recess can be used, such as triangular, square, or hexagonal. Coupling member 124 is accessible at an end of the body 112 opposite clamping members 14, 16 and enables data messages in serial form to be transmitted to and received from the surgical micro-clamping device 110 and the micro-clamping device 110 to be fully operated through the micro-clamping applicator. Coupling member 124 comprises a mounting platform 129 and electrodes for signals and power and a ground electrode (not shown).

With reference to FIGS. 13A-E, coupling member 124 of the threaded rod couples to and is driven by a connecting rod 126 of a micro-clamping applicator 128. Connecting rod 126 comprises a protrusion 127 having a shape complementary to the shape of the recess 125 in coupling member 124. Mounting guide 114 on body 112 aligns with and is received within recess 130 in arm 92 of the micro-clamping applicator 128 to ensure the micro-clamping device 110 is mounted to the micro-clamping applicator in the correct orientation. Electrodes 116, 118 of micro-clamping device 110 couple with respective electrodes 117, 119 of arm 92 of the micro-clamping applicator 128 to provide power to micro-clamping device 110 whilst coupled to the applicator 128. Rotational motion of connecting rod 126 is converted to linear motion of the threaded rod, which is connected to the actuation arms 122 which open and close the clamping members 14, 16.

Blood flow sensor array 30 continuously monitors the blood flow rate in the capillary in between the clamping members 14, 16 and transmits the information to the microcomputer of the applicator 128 for monitoring, logging, or control actions whilst the micro-clamping device 110 is coupled to the applicator 128.

Due to the threading mechanism of the linear micro-actuator 120, the threaded rod is not able to move upon detachment of the connecting rod 126 of the micro-clamping applicator 128 ensuring that the clamping members 14, 16 do not open or close beyond the set position during the operation.

At the conclusion of the operation, the micro-clamping applicator 128 is re-attached to the micro-clamping device 110. Connecting rod 126 rotates in an opposite direction enabling the threaded rod to move in the opposite direction resulting in the opening of the clamping members 14, 16.

The surgical micro-clamping device 110 can be made from any material or combination of materials suitable for surgical applications, as described herein in relation to other embodiments.

The micro-clamping applicator 128 shown in FIGS. 13A-E can have a similar configuration to the applicator 76 described in previous embodiments. Micro-clamping applicator 128 comprises body 78 providing a handle for the user, an embedded microcomputer 79 comprising a low-power microcontroller, on-board memory and digital and analogue input/output ports. Microcomputer 79 executes computer implemented code stored in the memory and controls operation of the applicator 128 in response to input from the user and/or feedback from the sensors. The microcomputer circuit can be assembled onto two small multilayer printed circuit boards mounted within the body 78 of the applicator 128 and is powered by an internal battery 81.

Output device in the form of graphic micro LED display 80 is provided on body 78 to display system messages, operation instructions, sensory data, battery information, diagnostic data, and other relevant information for effective user interaction. Body 78 comprises input devices in the form of push buttons 82, 84, 86, 88 and directional controller 90 in the form of a joystick or roller ball to control distal extension and retraction of connecting rod 126 located within cylindrical sleeve member 94 of arm 92 mounted to body 78.

Micro-clamping applicator 128 comprises a micro-motor 132 coupled to the microcomputer 79 and an actuation mechanism 134 coupled to the micro-motor 132. In some embodiments, the actuation mechanism is a threaded-nut-and-lead-screw actuation mechanism wherein a shaft of the micro-motor 132 comprises a lead screw and the inside of a connecting rod 126 is threaded. The micro-motor 132 and actuation mechanism 134 can be housed in the body 78 and/or in the cylindrical sleeve member 94. In response to inputs from the user, the microcomputer 79 controls movement of the connecting rod 126 via micro-motor 132 and actuation mechanism 134. Connecting rod 126 can be rotated bi-directionally in a clockwise or anticlockwise direction and can be extended or retracted whilst rotating.

Micro-clamping applicator 128 comprises an electromagnetic system which is controlled by the microcomputer 79. Connecting rod 126 can be magnetized and de-magnetized by the user using the push buttons 82, 84, 86, 88. When the user wants to connect the micro-clamping applicator 128 to surgical micro-clamp 110, the microcomputer 79 automatically detects the mounting by employing a conductance test through the electrodes 117, 119 in the cylindrical sleeve member 94 of arm 92 and electrodes 116, 118 in the body 112 of the micro-clamping device 110. The electromagnetic system is activated by the microcomputer 79 thus securing the micro-clamping device 110 into the micro-clamping applicator 128. Once the electromagnetic system is activated, control of the micro-clamping device 110 is managed through push buttons 82, 84, 86, 88 and directional controller 90 of micro-clamping applicator 128. Micro-clamping device 110 is manoeuvred into position around the blood vessel and clamped thereon as described above. Information from the blood flow sensor array 30 is relayed to the micro-clamping applicator 128 from the micro-clamping device 110 in real-time through electrodes 116, 117, 118, 119.

The electromagnetic system is de-activated by the user and the blood flow sensor 30 no longer receives power from the micro-clamping applicator 128 and is no longer monitored by the microcomputer 79 of the applicator. The applicator 128 can be disconnected from the micro-clamping device 110 by retracting connecting rod 126, disconnecting electrodes 116, 118 from electrodes 117, 119 and by disengaging mounting guide 114 from recess 130.

At the conclusion of the procedure/operation, the user positions connecting rod 126 of applicator 128 near coupling member 124 of micro-clamping device 110 and extends connecting rod 126 for engagement with coupling member 124. A rear portion of body 112 is received within cylindrical sleeve member 94 such that electrodes 116, 118 reconnect with electrodes 117, 119 and mounting guide 114 engages with recess 130. The electromagnetic system is re-activated by the microcomputer 79 to enable opening of clamping members 14, 16.

In view of the foregoing, it will be understood that, generally, embodiments of the present invention relate to surgical clamping devices that constrict or occlude blood flow in blood vessels during, for example, cardiac and general vascular surgery. This is achieved in at least some embodiments through the use of MEMS and/or Coriolis technology incorporated in the clamping device, which enables the elongate clamping members to sense the rate of blood flow through the respective blood vessel. The rate of blood flow is determined via a microchip/microcomputer circuit located internal or external to the surgical clamping device. When the blood flow has been occluded or constricted to the desired level, a braking system or limiter prevents the user of the device from tightening the elongate clamping members any further.

In view of the foregoing, it will also be understood that, generally, embodiments of the present invention also relate to tools for use with the improved surgical clamping devices. The tools, in the form of applicators 76, 128 as described herein, can be connected to, and disconnected from, surgical clamping devices 10, 110. Whilst connected, the improved surgical clamping devices can be maneuvered and controlled by the applicators, which enable the surgical clamping devices 10, 110 to be used and controlled in regions that are difficult to reach, such as deeper body cavities, or are obstructed.

Hence, another aspect of the invention is a surgical clamping kit comprising one or more of the surgical clamping devices 10 and one or more applicators 76 or one or more of the surgical clamping devices 110 and one or more applicators 128.

It will be appreciated that combinations of the embodiments described herein fall within the scope of the present invention. For example, it is envisaged that one or more of the features of the embodiments described above with reference to FIGS. 1 to 5C can be combined with one or more of the features of the embodiments described above with reference to FIGS. 6A to 13E. For example, in the embodiments described above with reference to FIGS. 6A to 13E, clamping members 14, 16 can be made from a flexible material allowing the shape of the clamping members 14, 16 to be adjusted. In such embodiments, alternatively or additionally, the angle of the clamping members 14, 16 relative to the body 12 can be adjustable. Clamping members 14, 16 can alternatively or additionally comprise one or more of the projections 40, recesses 42, inclined portion 44 and/or magnifying device 50.

Hence, embodiments of the present invention provide solutions for alleviating at least some of the problems of the prior art. Embodiments of the improved surgical clamping devices 10 comprise elongate clamping members 14, 16 having an adjustable shape enabling the clamping members to be shaped according to the blood vessel being clamped and/or according to the surgical procedure being performed. Embodiments of the improved surgical clamping devices 10 comprise elongate clamping members 14, 16 wherein the angle of the clamping members relative to the body 10 is adjustable in a vertical and/or horizontal plane. These embodiments enable the improved surgical clamping devices 10 to be suitable for use in a wider range of surgical procedures and for a wider variety of types, calibres and masses of blood vessels. For example, a single embodiment of the improved surgical clamping device described herein can be suitable for constricting and occluding blood flow in blood vessels having a diameter in the range of about 0.2 mm to about 7.0 mm. Hence, the need for an extensive range of clamping devices applicable to only a few procedures is obviated.

Embodiments comprising the blood flow sensor and/or mass sensor enable the level of constriction of the blood vessel and the point at which the blood vessel is occluded to be accurately detected. This prevents excessive pressure from being applied to the blood vessel whilst ensuring that occlusion has occurred before commencing with the next stage of the surgical procedure. Similarly, the blood flow sensor enables the resumption of blood flow to be accurately controlled after the procedure has been carried out. The blood flow sensor and/or mass sensor also enable the calibre of the blood vessel to be assessed. Hence, the risk of surgical procedures can be reduced. The risk associated with clamping veins/arteries/capillaries is also reduced by the provision of the projections 40 and recesses 42 which prevent the clamping members closing beyond a predefined limit and thus from exerting an excessive pressure on the vein/artery/capillary.

The provision of a non-slip coating or layer 34 on one or both of the elongate clamping members 14, 16 prevents the blood vessel 18 from sliding from a clamping surface of the elongate clamping members, thus providing greater control during the surgical procedure. Features such as the channel 36, the inclined surface 44, the enlarged wall 46 and the magnifying device 50 also facilitate quicker and more accurate location of the blood vessel and/or more reliable clamping of the blood vessel compared with at least some of the prior art clamping devices.

Embodiments comprising detachable elongate clamping members 14, 16 provide an improved surgical clamping kit which is adaptable to a wide range of surgical procedures and the clamping of a variety of blood vessels. The detachable elongate clamping members can be single use or reusable and can be selected as required for the particular procedure. Embodiments comprising the body 12 having a controller 20, and in particular the MEMS fabricated body, provide a reusable body that can accurately control the separation of, and thus the pressure exerted by, the elongate clamping members. The body can be detached once the desired clamping pressure has been attained and re-attached to the elongate clamping members to release the elongate clamping members and resume blood flow.

Provision of an output device 32, such as an LCD screen or seven segment display, provides the user with an instant indication of the blood flow, irrespective of whether the output device 32 is provided on the improved surgical clamping device 10 or as part of a separate medical monitoring device. Wireless communication avoids the need for external cables or wires that may snag on other objects during surgical procedures.

Applicators 76, 128, enable the surgical clamping devices 10, 110 to be used and controlled at a distance, for example, in regions that are difficult to reach, such as deeper body cavities, or are obstructed.

In this specification, the terms "comprise", "comprises", "comprising" or similar terms are intended to mean a non-exclusive inclusion, such that a system, method or apparatus that comprises a list of elements does not include those elements solely, but may well include other elements not listed.

Throughout the specification the aim has been to describe the preferred embodiments of the invention without limiting the invention to any one embodiment or specific collection of features. It is to be appreciated by those of skill in the art that various modifications and changes can be made in the particular embodiments exemplified without departing from the scope of the present invention.

The invention claimed is:

1. An apparatus comprising a surgical clamping device and a handheld applicator,
   the surgical clamping device comprising:
      a clamping device body comprising a mounting member for coupling the surgical clamping device to the applicator; and
      a pair of clamping members extending from the clamping device body;
   the handheld applicator comprising:
      an applicator body forming a handle for holding by a user;
      an arm connected to the applicator body at a proximal end; and
      a pan tilt head at a distal end of the arm, the pan tilt head comprising an interface to releasably connect the pan tilt head to the mounting member of the surgical clamping device;
   wherein:
   the applicator body houses at least one input device, at least one output device and a microcontroller coupled to the at least one input device and the at least one output device;
   the pan tilt head and at least one of the clamping members are controlled via the microcontroller of the applicator in response to one or more inputs from a user via the at least one input device; and
   the surgical clamping device comprises an electronic controller housed within the clamping device body and coupled to control movement of at least one of the clamping members to control a pressure exerted by the clamping members on a blood vessel clamped therebetween.

2. The apparatus of claim 1, wherein the surgical clamping device comprises:
   a micro-motor coupled to the electronic controller;
   a power supply coupled to the micro-motor and the electronic controller; and
   a micro-gearbox coupled to the micro-motor and to at least one of the clamping members.

3. The apparatus of claim 1, wherein the clamping device body comprises an arcuate platform for receiving the blood vessel.

4. The apparatus of claim 1, wherein one or more of the clamping members comprises one or more of the following on at least part thereof:
- a non-slip coating;
- a soft cushioning layer;
- a channel for receiving the blood vessel, the channel comprising a central ridge;
- a projection aligned with a recess in the other clamping member to determine a minimum separation for the clamping members;
- an inclined portion for receiving the blood vessel;
- a magnifying device coupled to one of the clamping members.

5. The apparatus of claim 1, wherein the clamping members are one or more of the following:
- elongate;
- tapered;
- made from a flexible material allowing the shape of the clamping members to be conformed to a blood vessel to be clamped;
- integrally formed with the clamping device body;
- detachable from the clamping device body;
- adjustable relative to the body in a vertical plane and a horizontal plane.

6. The apparatus of claim 1, wherein the clamping members occupy one of the following:
- a plurality of predetermined angles relative to the clamping device body;
- any position within a predetermined range of angles.

7. The apparatus of claim 1, wherein:
a length of the elongate clamping members is selectable from a plurality of predetermined lengths.

8. The apparatus of claim 1, wherein the clamping device body comprises one or more electrodes for connection to respective electrodes of the applicator.

9. The apparatus of claim 1, wherein the arm comprises:
a cylindrical sleeve member connected to the body;
an elongation member housed within the cylindrical sleeve member; and
a linear actuator for controlling extension and retraction of the elongation member relative to the cylindrical sleeve member; and
a locking mechanism in the cylindrical sleeve member to prevent the elongation member from sliding out of the sleeve member.

10. The apparatus of claim 1, wherein the head comprises a frame supporting a ball member which can pan and tilt relative to the frame, the ball member comprising an interface for coupling the surgical clamping device to the head.

11. The apparatus of claim 1, comprising at least one micro-motor in the head to control the orientation and position of the surgical clamping device attached to the head, wherein the arm is flexible.

12. The apparatus of claim 1, comprising an electromagnetic system controlled by the microcontroller for controlling connection and disconnection of the surgical clamping device and the applicator.

13. The apparatus of claim 1, wherein:
the elongate clamping members or the clamping device body are disposable or are reusable.

14. The apparatus of claim 1, wherein the arm comprises:
a cylindrical sleeve member connected to the body;
an elongation member housed within the cylindrical sleeve member; and
a linear actuator for controlling extension and retraction of the elongation member relative to the cylindrical sleeve member; or
a locking mechanism in the cylindrical sleeve member to prevent the elongation member from sliding out of the sleeve member.

15. The apparatus of claim 1, comprising at least one blood flow sensor mounted to at least one of the clamping members to detect blood flow in the blood vessel.

16. The apparatus of claim 15, wherein the clamping members either side of the blood vessel are locked in place once the at least one blood flow sensor detects that blood flow has been occluded or constricted to a desired extent.

17. The apparatus of claim 15, wherein the at least one output device comprises an output device for displaying information relating to the surgical clamping device, including an indication of the blood flow measured by the at least one blood flow sensor.

18. The apparatus of claim 1, comprising at least one sensor mounted to at least one of the clamping members to detect one or more of the following characteristics of the blood vessel clamped between the clamping members: a calibre of the blood vessel; a thickness of a wall of blood vessel; a mass of the blood vessel.

19. The apparatus of claim 18, wherein the electronic controller adjusts a pressure applied by the clamping members according to the detected calibre, wall thickness or mass of the blood vessel.

* * * * *